United States Patent
Porgador et al.

(10) Patent No.: US 9,861,686 B2
(45) Date of Patent: Jan. 9, 2018

(54) DIAGNOSTIC AND THERAPEUTIC METHODS AND THEIR APPLICATION IN AMYOTROPHIC LATERAL SCLEROSIS (ALS)

(71) Applicant: Ben-Gurion University of the Negev Research and Development Authority, Beer Sheva (IL)

(72) Inventors: Angel Porgador, Lehavim (IL); Rachel Lichtenstein, Beer Sheva (IL)

(73) Assignee: Ben-Gurion University of the Negev Research & Development Authority, Beer Sheva (IL)

( * ) Notice: Subject to any disclaimer, the term of this patent is extended or adjusted under 35 U.S.C. 154(b) by 0 days.

(21) Appl. No.: 14/361,806

(22) PCT Filed: Dec. 4, 2012

(86) PCT No.: PCT/IL2012/050510
§ 371 (c)(1),
(2) Date: May 30, 2014

(87) PCT Pub. No.: WO2013/084236
PCT Pub. Date: Jun. 13, 2013

(65) Prior Publication Data
US 2014/0328824 A1  Nov. 6, 2014

Related U.S. Application Data

(60) Provisional application No. 61/566,697, filed on Dec. 5, 2011.

(51) Int. Cl.
*A61K 38/47* (2006.01)
*A61K 31/428* (2006.01)
*C07K 16/42* (2006.01)
*G01N 33/68* (2006.01)
*C07K 16/00* (2006.01)

(52) U.S. Cl.
CPC ........... *A61K 38/47* (2013.01); *A61K 31/428* (2013.01); *C07K 16/00* (2013.01); *C07K 16/4283* (2013.01); *G01N 33/6854* (2013.01); *G01N 33/6896* (2013.01); *C07K 2317/41* (2013.01); *C07K 2317/52* (2013.01); *C07K 2317/732* (2013.01); *G01N 2800/28* (2013.01)

(58) Field of Classification Search
CPC .. A61K 38/47; A61K 31/428; C07K 16/4283; C07K 16/00; C07K 2317/41; C07K 2317/52; G01N 33/6854; G01N 2800/28
See application file for complete search history.

(56) References Cited

U.S. PATENT DOCUMENTS

7,351,686 B2 * 4/2008 Eisenbach-Schwartz ........................ A61K 39/0007 424/185.1
2009/0305308 A1 * 12/2009 Schubert .................. B82Y 5/00 435/7.21
2010/0143353 A1 6/2010 Mosser et al.

FOREIGN PATENT DOCUMENTS

WO 03/048773 A2 6/2003
WO 2010/012106 A1 2/2010
WO 2011/140640 A1 11/2011

OTHER PUBLICATIONS

Williams J. R. et al., "Copper delivery to the CNS by CuATSM effectively treats motor neuron disease in SODG93A mice co-expressing the Copper-Chaperone-for-SOD", Neurobiology of Disease, Jan. 2016, vol. 89, pp. 1-9.*
Jefferis R et al: "Evaluation of monoclonal antibodies having specificity for human IgG subclasses: results of the 2nd IUIS/WHO collaborative study". Immunology Letters. Elsevier BV. NL. vol. 31. No. Feb. 1, 1992 (Feb. 1, 1992). pp. 143-168. XP023691733. ISSN: 0165-2478. 001:10.1016/0165-2478(92)90141-A [retrieved on Feb. 1, 1992] abstract table 1.
J. Simon Lunn et al: "Vascular endothelial growth factor prevents G93A-SOD1-induced motor neuron degeneration". Developmental Neurobiology. vol. 69. No. 13. Nov. 1, 2009 (Nov. 1, 2009). pp. 871-884. XP055053219. ISSN: 1932-8451, 001: 10.1002/dneu. 20747 abstract.
Mario Rafael Pagani et al: "Autoimmunity in Amyotrophic Lateral Sclerosis: Past and Present" Neurology Research International. vol. 53. No. 6. Jan. 1, 2011 (Jan. 1, 2011). pp. 1239-1211. XP055053223. ISSN: 2090-1852. 001: 10.1371/journal.pone.0001254 abstract.
Meital Edri-Brami et al: "Glycans in Sera of Amyotrophic Lateral Sclerosis Patients and Their Role in Killing Neuronal Cells". PLOS One. vol. 7. No. 5. Jan. 1, 2012 (Jan. 1, 2012) p. e35772. XP055053113. ISSN: 1932-6203. 001: 10.1371/journal.pone. 0035772 the whole document.
Int'l Search Report for PCT/IL2012/050510 dated Feb. 21, 2013.

* cited by examiner

*Primary Examiner* — Satyendra K Singh
(74) *Attorney, Agent, or Firm* — Cooley LLP; Ivor R. Elrifi; Matthew Pavao

(57) ABSTRACT

The present invention provides a method of treating, delaying the onset, delaying progression of, reducing the incidence of or reducing the severity of amyotrophic lateral sclerosis in a subject, the method comprising administering to a subject an agent, which interferes with IgG-A2BG2 expression, IgG-A2BG2 function or IgG-A2BG2 interaction with CD16 in said subject.

3 Claims, 11 Drawing Sheets

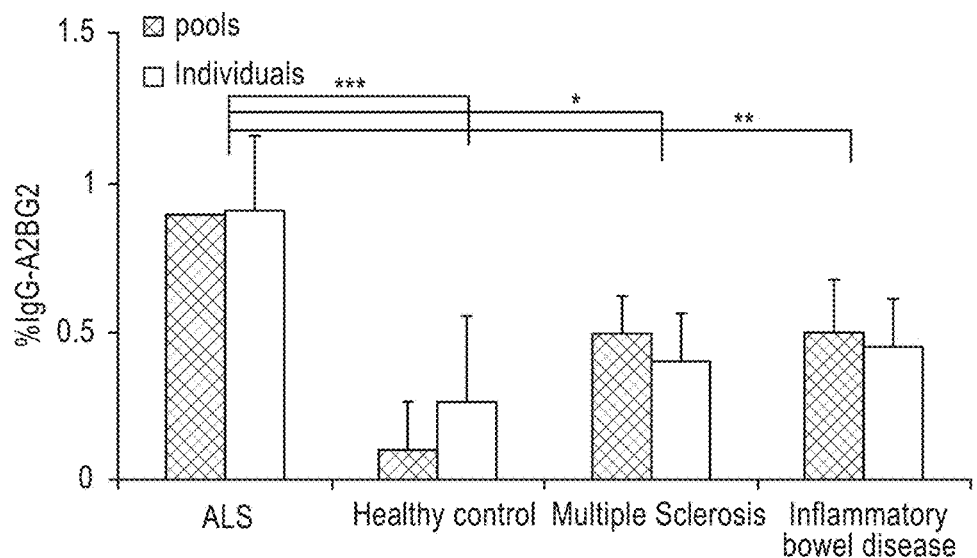
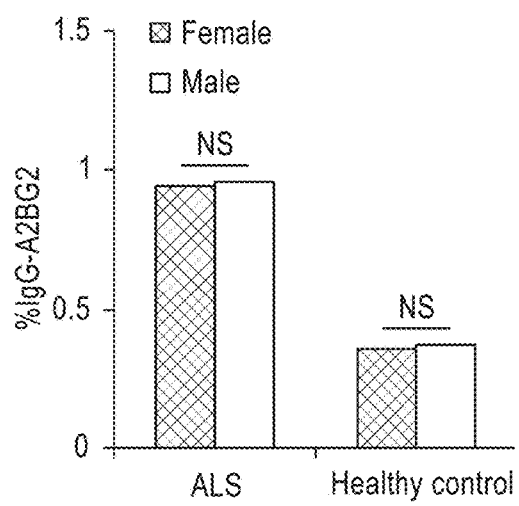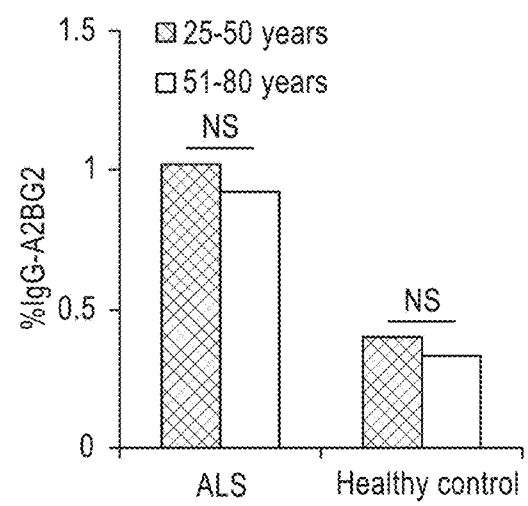

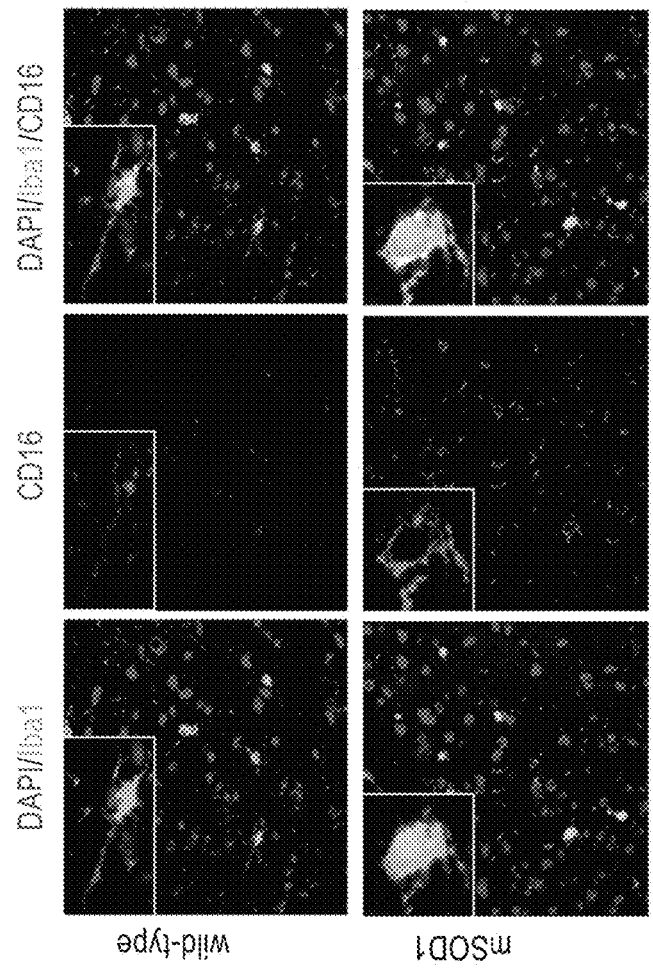
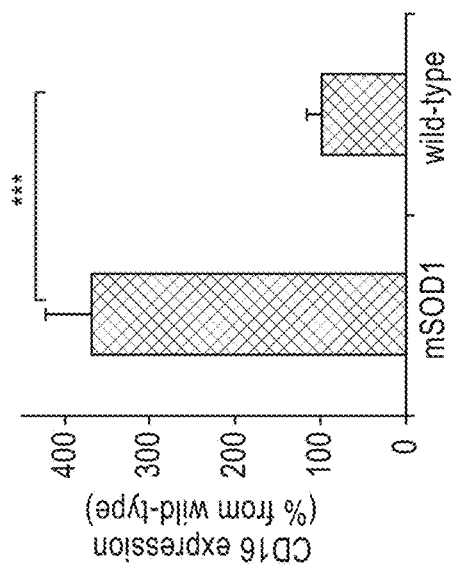
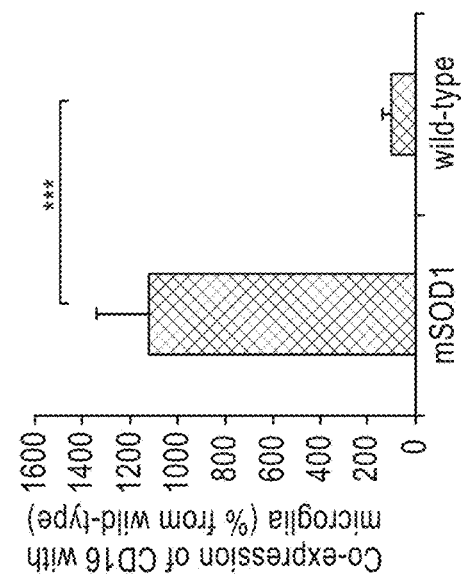
Figure 4A
Figure 4B
Figure 4C

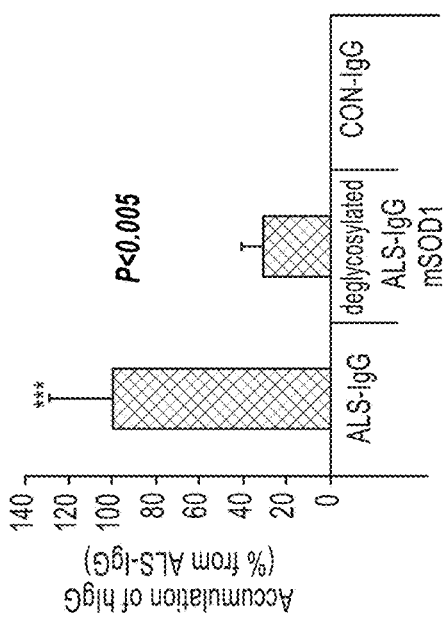
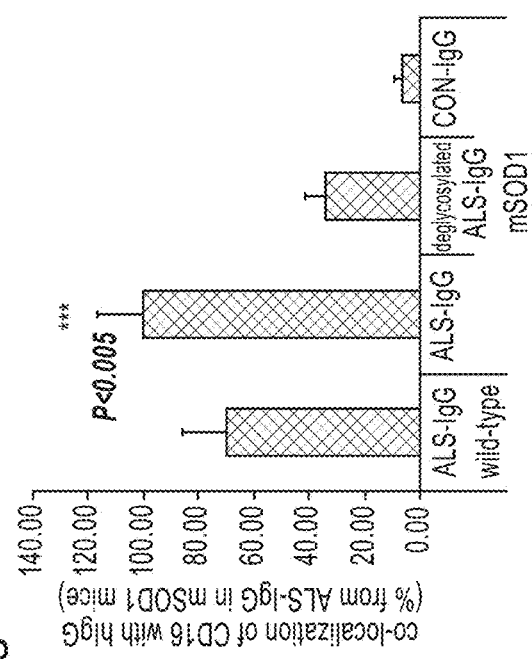
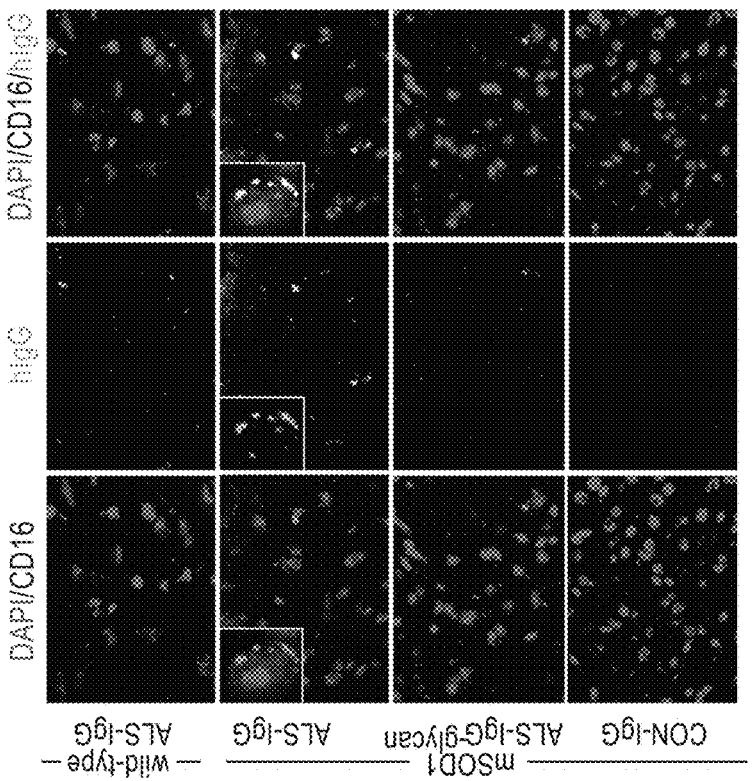
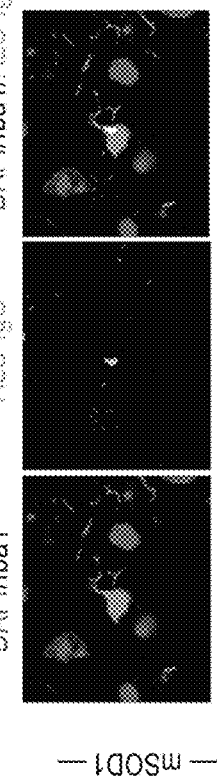

US 9,861,686 B2

DIAGNOSTIC AND THERAPEUTIC METHODS AND THEIR APPLICATION IN AMYOTROPHIC LATERAL SCLEROSIS (ALS)

BACKGROUND TO THE INVENTION

Immunoglobulins, the major secretory products of the adaptive immune system, include the IgG subclass, which identifies and neutralizes foreign cells. As adaptors, IgG activate an immune response by simultaneously binding antigens through their variable domains (F(ab)2) and through interaction of their Fc domain with Fcγ receptors (FcγR) on immune cells. The human FcγR family consists of the activating receptor FcγRIIIA (CD16) that mediates antibody-dependent cellular cytotoxicity (ADCC). The binding of IgG to CD16 is sensitive to the presence of glycosylation at a single site on asparagine 297 ($N^{297}$) in its Fc domain, with a loss of binding observed after cleaving or preventing Fc glycosylation. The nature of the glycans attached to $N^{297}$ varies the affinity of the CD16 interaction and thus governs antibody cytotoxicity. It has been suggested that IgG play a role in motor neuron degeneration. This was based on the finding of IgG deposit on the spinal cord and brain of patients with amyotrophic lateral sclerosis (ALS) and in animal models of inherited ALS. It was further found in animal models, that IgG from ALS patients could not be up-taken by motor axon terminals, after removing the IgG Fc domain. Consequently, it appears that FcγRs are involved in IgG deposition or in uptake by motor neurons.

ALS is a fatal neurodegenerative disease caused by degeneration of the upper and lower motor neurons. ALS patients and animal models of inherited ALS, like mutant Cu/Zn superoxide dismutase (mSOD1), display similar inflammatory responses at the site of the motor neuron injury, enabling both the CNS resident and systemic inflammatory cells to balance between neuroprotection and neurotoxicity. One population involved in these inflammatory responses is microglia cells, which during their activation change morphology, surface receptor expression, and produce growth factors and cytokines, leading to neuron protection or injury depending on the physiological conditions. The manners in which the signals switch between protective to cytotoxic microglia are not yet fully understood. However, ALS progression is attributed, in part, to cytotoxic microglia cells, which secrete proinflammatory cytokines leading to neuron damage. Cumulative, data demonstrate that Toll-like receptors or T-cells interacting with microglia are involved in inducing cytotoxic microglia, but data relating FcγR to microglia activity in ALS are scarce. Notably, the data known so far link the FcγR to phagocytosis by activated microglia in other neurodegenerative diseases, like Alzheimer's disease.

It would be beneficial to have an effective and selective treatment for ALS, which is as yet unavailable.

SUMMARY OF THE INVENTION

The present invention established that over-expression of CD16 on activated microglia can increase the incidence of binding ALS-produced IgG through an Fc glycan, A2BG2, thereby inducing neuron loss.

In some embodiments, this invention provides a method of treating, delaying the onset, delaying progression of, reducing the incidence of or reducing the severity of amyotrophic lateral sclerosis in a subject, said method comprising administering to a subject an agent, which interferes with IgG-A2BG2 expression, IgG-A2BG2 function or IgG-A2BG2 interaction with CD16 in said subject.

In some embodiments, the invention provides a method of diagnosing amyotrophic lateral sclerosis (ALS) in a subject in need thereof, the method comprising determining a relative increase in IgG-A2BG2 expression in a sample of said subject as compared to a normal or baseline expression value wherein said relative increase is indicative of said subject suffering from or predisposed to ALS, thereby being a method of diagnosing ALS in said subject.

In some embodiments, the invention provides a kit for diagnosing ALS comprising antibodies capable of specifically binding to IgG-A2BG2.

BRIEF DESCRIPTION OF THE DRAWINGS

FIG. 3 The Fc domain of ALS-derived IgG contains a galactosylated $N^{297}$ glycan with bisecting GlcNAc and lacking a core fucose (A2BG2). Paired Student's t-test analysis of glycan amounts in individual or in pooled serum samples of healthy controls and inflammatory bowel disease, multiple sclerosis and ALS patients indicates that the A2BG2 structure (peak no. 7) is a statistically unique $N^{297}$ glycan of ALS-derived IgG (A), Paired Student's t-test analysis of A2BG2 with respect to gender (B) and age (C). Data represent means±SD of measurements of 19 ALS, 24 healthy controls, 22 inflammatory bowel disease patients, and 6 multiple sclerosis patients or 6 pools generated by mixing 4 individual serum samples from every group (in multiple sclerosis 2 pools were generated by mixing 3 individual serum samples). Statistical significance, * $p<0.005$,  $p<0.01$ and *, $p<0.05$, versus the appropriate control.

FIG. 4 Expression of CD16 and co-expression of CD16 with microglia of G-93A-SOD1 brain tissue. Representative confocal microscopic images of brain cortex slices taken from 130-day old G-93A-SOD1 mice and age-matched littermates stained for CD16, Iba1 (microglia), and counterstained with nuclear DAPI (A). The boxed area in A is a high magnification of CD16-positive microglia (small images in the merged images, A, left). The histogram shows the expression of CD16 in brain tissues of mSOD1 relative to wild-type mice (in 8 μm brain slices). The significant differences between mSOD1 and wild-type mice, verify the increased expression of CD16 at the end-stage of ALS disease in mSOD1 mice (B). The histogram shows the co-expression of CD16 with microglia in mSOD1 relative to wild-type mice (C). The quantity of CD16 was analyzed by measuring red intensity per defined area and the quantity of CD16 co-expressed with Iba1 was analyzed by measuring % of red intensity on a defined green intensity area. The measurements were performed on 5 fields from 3-4 sections per mouse. Error bars indicate means±SD. The P value analysis * p<0.005,  p<0.01 and * p<0.05, versus non-SOD1 littermates represents a comparison with a Student's t-test.

FIG. 8 B shows Rituximab's Fc coupling to FcγRIIIA-transfected BW cell line results in secretion of cytokines; CD16-transfected BW cells were incubated overnight with intact or rituximab's Fc and PNGase-F-treated rituximab's Fc domain in serum free RPMI. The figure illustrates secretion of IL-2 by BW cells in response to interactions with rituximab and rituximab's Fc domain.

DETAILED DESCRIPTION OF THE INVENTION

Figure 1:
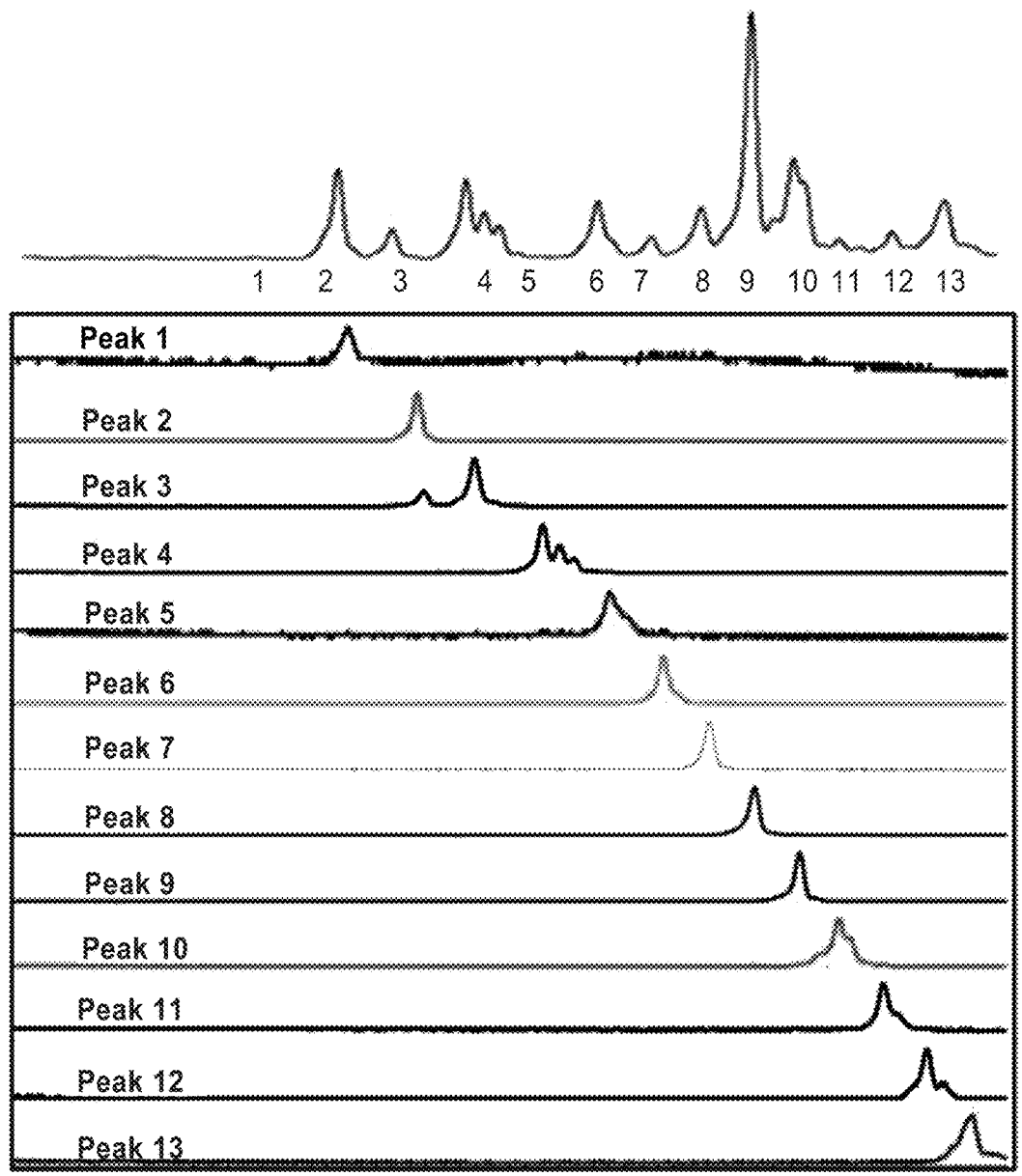
FIG. 1 Fractions of whole serum N-glycans. The total N-glycans from individual samples of ALS patients or healthy volunteers were fractionated by quantitative normal phase HPLC, according to glucose units (GU). The thirteen observed fractions were numbered, and each was pooled and subsequently digested by exoglycosidase to determine glycan structures and amounts.

In some embodiments, this invention provides a method of treating, delaying the onset, delaying progression of, reducing the incidence of or reducing the severity of amyotrophic lateral sclerosis in a subject, said method comprising administering to a subject an agent, which interferes with IgG-A2BG2 expression, IgG-A2BG2 function or IgG-A2BG2 interaction with CD16 in said subject.

Using an N-glycome approach and tissue stains, overexpression of CD16 was demonstrated herein on activated microglia and co-localization of ALS-IgG with CD16 in sections of brain tissue from G93A-SOD1 mice was shown. In vitro activities of intact ALS-IgG with this Fc glycan, including its role in ADCC against neuroblastoma cells was demonstrated, as well. Localization of intact ALS-IgG in the immunological synapse between microglia and the neuron of G93A-SOD1 brain tissue was demonstrated, reinforcing the mechanistic involvement of in vivo ADCC in the pathogenesis of ALS. The synapse was generated between human-IgG and microglia and the neurons in mice.

As demonstrated herein, the structure A2BG2 is present in the Fc-N$^{297}$ of ALS-IgG. This glycan increases IgG affinity for CD16 on effector cells, consequently enhancing ADCC and therefore being an important element in ALS pathogenesis.

Therefore, glycans of ALS-IgG may serve as a biomarker and may be involved in neuronal damage.

In some aspects of this invention and representing some embodiments thereof, the invention provides for a therapeutic method for treating, delaying the onset, delaying progression of, reducing the incidence of or reducing the severity of amyotrophic lateral sclerosis (ALS), which exploits the finding that A2BG2 is proportionately present in the Fc-$N^{297}$ of ALS-IgG at higher levels than in normal subject IgG.

According to one aspect, the invention provides a method whereby a subject suffering from or predisposed to the development of ALS is administered an agent, which interferes with IgG-A2BG2 expression, IgG-A2BG2 function or IgG-A2BG2 interaction with CD16 in such subject.

In some embodiments, such an agent is a selectively expressed enzyme which cleaves the A2BG2 glycan or part of the A2BG2 glycan (for example, mono sugars) from the Fc portion of IgG molecules in the subject.

In some embodiments, such an agent is an antibody with appropriate specificity for the A2BG2 portion of the IgG or a competing molecule, containing the A2BG2 glycan (for example, Fc conjugated to A2BG2), which in turn may interfere with the binding of the CD16 receptor to IgG antibodies in the subject, at a site which contributes to the pathogenesis of ALS or ALS development in said subject, thereby serving as a therapeutic method.

Antibodies exist as full length intact antibodies or as a number of well-characterized fragments produced by digestion with various peptidases or chemicals. Thus, for example, pepsin digests an antibody below the disulfide linkages in the hinge region to produce F(ab')$_2$, a dimer of Fab which itself is a light chain joined to VH-CH1 by a disulfide bond. The F(ab')2 may be reduced under mild conditions to break the disulfide linkage in the hinge region thereby converting the F(ab')2 dimer into an Fab' monomer. The Fab' monomer is essentially a Fab fragment with part of the hinge region. (See FUNDAMENTAL IMMUNOLOGY, W. E. Paul, ed., Raven Press, N.Y. (1993), for a more detailed description of other antibody fragments.) While various antibody fragments are defined in terms of the digestion of an intact antibody, one of skill will appreciate that any of a variety of antibody fragments may be synthesized de novo either chemically or by utilizing recombinant DNA methodology. Thus, the term antibody, as used herein also includes antibody fragments either produced by the modification of whole antibodies or synthesized de novo or antibodies and fragments obtained by using recombinant DNA methodologies. Antibody fragments produced by recombinant techniques may include fragments known by proteolytic processing or may be unique fragments not available or previously known by proteolytic processing. Whole antibody and antibody fragments also may contain natural as well as unnatural amino acids. The term "antibody" also encompasses chimeric forms of antibody, CDR grafted antibody and other humanized forms of non-human antibodies.

Recombinant antibodies can include alterations in the amino acid sequence to provide for desired characteristics, for Example changes can be made in the variable region to provide improved antigen binding characteristics.

In some embodiments, such an agent may be a selectively expressed enzyme which cleaves the A2BG2 glycan from the Fc portion of IgG molecules in said subject.

In some embodiments, such an agent may be any appropriate agent, which can be readily developed by the skilled artisan, such as, for example, plant lectins, soluble animal lectins, soluble domains of membrane receptors that bind the A2BG2 portion of the IgG.

In some embodiments, such an agent may be any appropriate agent, which specifically binds the Fc portion of the IgG, or a bulky region on the IgG, and thereby interferes with CD16 binding to IgG-A2BG2.

In some embodiments, such an agent may be any appropriate agent, which specifically binds the IgG-A2BG2 containing antibody/antigen complex, for example, and may further contain a bulky region, thereby interfering with CD16 binding.

In some embodiments, the antigen specifically recognized by the Fab domain, represents a target for design in accordance with the principles disclosed herein.

In some embodiments, such an agent may include part of an antibody (for example, an Fab fragment) with appropriate specificity for the Fc, which in turn may interfere with the binding of CD16 receptor.

It will be appreciated that interfering with IgG-A2BG2 expression, IgG-A2BG2 function or IgG-A2BG2 interaction with CD16 in such subject may be accomplished using any of the inhibitors as described hereinabove.

In some embodiments, the term "treatment" refers to any method used to alleviate, delay onset, reduce severity or incidence, or yield prophylaxis of one or more symptoms or aspects of a disease, disorder, or condition. For the purposes of the present invention, treatment can be administered before, during, and/or after the onset of symptom. In some embodiments, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

In some embodiments, such agents may be delivered via any means, for example, intravenously, parenterally, intranasally, intraocularly, topically, or via any other appropriate delivery route.

It will be appreciated by the skilled artisan, that such agents may be best prepared to specifically target the central nervous system and therefore to cross the blood-brain barrier. Various methods exist to render such an agent as capable of crossing the blood-brain barrier and such modification is envisioned as being a part of this invention. For example, and in some embodiments, the agent may be modified as described in U.S. Pat. No. 7,557,182, U.S. Pat. No. 5,187,158, WIPO Patent Application WO/1994/002178, each of which is fully incorporated by reference herein, and others, as will be appreciated by the skilled artisan.

In some embodiments, the subject is administered adjunct therapies to ameliorate the symptoms of ALS.

Current treatment modalities for ALS include but are not limited to, FDA approved medications such as Riluzole (Rilutek). Riluzole is believed to reduce damage to motor neurons by decreasing the release of glutamate via activation of glutamate transporters. In addition, the drug offers a wide array of other neuroprotective effects, by means of sodium and calcium channel blockades, inhibition of protein kinase C, and the promotion of NMDA (N-methyl d-aspartate) receptor antagonism. In addition to the use of medical intervention to treat ALS, there are other approaches applied for ALS patients. These include mind body methods, holistic problem solving methods, psychotherapy, hypnotherapy and nutrition related methods.

In some embodiments, ALS generally presents with a characteristic pattern of lesions involving motor neurons of the brain stem and anterior horn area of the spinal cord. There is also involvement of the large pyramidal neurons of the motor cortex, with pathological changes found in the extramotor cortex, in the cerebrospinal and sensory systems as well as in the subcortical regions. The criteria for diagnosis of ALS have been established by the World Federation of Neurology (Brooks, B. R., 1994, El Escorial World Federation of Neurology criteria for the diagnosis of amyotyrophic lateral sclerosis. Subcomittee on Motor Neurone Diseases/Amyotrophic Lateral Sclerosis of the World Federation of Neurology Research Group on Neuromuscular Diseases and the El Escorial 'Clinical limits of amyotrophic lateral sclerosis' workshop contributors. J. Neurol Sci [Suppl] 124:96-107).

ALS is characterized by paralysis, muscular atrophy, spasticity, and a variety of other motor signs. The natural history of ALS is well documented. The presenting symptoms of ALS include, for example, muscle wasting or weakness of the hands or legs. Occasionally, cramps and fasciculations precede the common presenting symptoms. Bulbar symptoms consisting of dysarthria or dysphagia appear as the disease progresses, but can also be the presenting complaints in some of the patients. Such patients may be placed on a prophylactic regimen as long as risk remains high as determined by standard diagnostic indicators, the method being that which is described herein.

A patient or tissue may also be treated by the method of the invention after some damage due to ALS has occurred to minimize further damage from additional neuropathological events.

A patient presenting with symptoms indicative of ALS may also be treated by the method of the invention to prevent progression of the disease or to prevent the development of more severe symptoms. A patient with ALS may also be treated by the method of the invention to lessen the symptoms of ALS and/or to extend the patient's longevity.

One or more of the following clinical evaluations can be used to assess progress/prevention of ALS disease.

(1) Quantitative Strength and Functional markers: The TUFTS Quantitative Neuromuscular Examination (TQNE) is a well standardized, reliable, validated test to measure strength and function in ALS. The test involves measurement of maximum voluntary isometric contraction (MVIC) of 8 muscle groups in the arms using a strain gauge tensiometer. This measurement is a standard for clinical trials in ALS.

(2) Functional measures: The ALS Functional Rating Scale (ALSFRS) is an easily administered ordinal rating scale used to determine patients'assessment of their ability and independence in 10 functional activities. Validity has been established by correlating ALSFRS scores with change in strength over time. The ALSFRS is generally a secondary outcome measure in clinical trials.

(3) Measures of Upper Motor Neuron Function by traditional methods.

In some embodiments, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

In some embodiments, the invention provides a method of diagnosing amyotrophic lateral sclerosis (ALS) in a subject in need thereof, the method comprising determining a relative increase in IgG-A2BG2 expression in a sample of said subject as compared to a normal or baseline expression value wherein said relative increase is indicative of said subject suffering from or predisposed to ALS, thereby being a method of diagnosing ALS in said subject.

In some embodiments, the invention provides a method of diagnosis for an individual suspected of having sporadic or familial ALS. In some embodiments, the term, an "individual suspected of having sporadic or familial ALS" refers to an individual with one or more ALS symptoms. Such an individual may also have a family history of ALS and may have a wild-type or a mutant SOD-1 protein sequence. Family history is preferably immediate family members including parents and siblings. Family history also may include grandparents.

In some embodiments, the sample is serum or plasma. In some embodiments, the sample is cerebrospinal fluid (CSF).

In some embodiments, determining a relative increase in IgG-A2BG2 expression in a sample is effected by NP-HPLC or MALDI-TOF MS, or in some embodiments, an ELISA or RIA may be developed, that will specifically detect relative or absolute increases in IgG-A2BG2 expression in a sample In some embodiments, the method further comprises substantiating the method of diagnosing ALS in said subject by using a diagnosis method selected from the group consisting of electromyography, nerve conduction velocity magnetic resonance imaging (MRI) and bio-molecular analysis.

In some embodiments, the invention provides a kit for diagnosing ALS comprising antibodies, or other agents capable of specifically binding to IgG-A2BG2, whose binding can be qualitatively assessed.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements. Various embodiments and aspects of the present invention as delineated hereinabove and as claimed in the claims section below find experimental support in the following examples.

EXAMPLES

Materials and Methods

Human subjects: Experimental procedures involving human subjects were conducted in conformance with the policies and principles contained in the Helsinki Declaration according to National Health Regulations (Medical Experimentation in Human Beings, 1980), and in accordance with GCP-ICH regulations. This study was approved by both the Sourasky and Soroka Medical Center Helsinki Committees. Sera were collected from 19 ALS patients (11 males). The average patient age at sampling was 60±1.3 years (range 28-80) and the average duration of the disease was 26±13 months (range 9-54). Two patients had familial ALS. There was a relatively high incidence of bulbar-onset patients in our sample (9-47%). The average disability of the patients at the time of the examination, as measured by the ALSFRS-R score was 34±7 (range 17-44).

For control experiments, sera were collected from 24 healthy subjects (13 males) with an average age of 48±11 years. As non-ALS disease controls, sera were taken from 22 patients (12 males) with inflammatory bowel disease, with an average age of 44±14 years. Ten patients had Crohn's disease and the rest suffered from ulcerative colitis. As an additional control for neurodegenerative disease, sera were taken from 6 patients with multiple sclerosis with an average age of 42±17 years.

Blood collection and analysis: The collected blood samples were collected in 10 ml SST Vacutainers (BD) and allowed to clot at 4° C. for 30 min. Coagulated blood was spun at 3,000 rpm for 10 minutes, and the serum portion was immediately aliquoted to 50 µl in low-binding vials and frozen for storage at −80° C. until thawed for glycomic and immunologic analyses. The aliquots were coded by Sourasky hospital, where the information about the samples was not available to the laboratory research assistants. Two research assistants carried out the glycomic experiments. One assistant used the individual and pooled samples, the other used the individual samples, providing two independent experiments.

Glycan separation and normal phase HPLC analysis: In accordance with previous procedure (Küster, B., et. al. (1997). Anal. Biochem. 250, 82-91), PNGase-F-released glycans (Roche Diagnostics, Germany) from 50 □l of serum were fluorescently labeled with 2-aminobenzamide (2-AB), by reductive amination. The glycans were subsequently separated on a 4.6×250 mm Glyco-Sep N column (Waters, Milford, Mass.) using two Waters 510 pumps, a Waters 717 auto-injector, and a FP-920 fluorescent detector (Jasco, Easton, Md.). The solvents used were buffer A (50 mM ammonium formate, pH 4.4) and buffer B (acetonitrile). The glycans were eluted by a linear gradient of buffer A, such that initial conditions were 20% buffer A at a flow rate of 0.4 ml/min. The concentration of buffer A was changed from 35-53% (the rest was buffer B) over 132 min, and then from 53-100% (the rest was buffer. B) over the next 3 min, at a constant flow rate. The column was washed with 100% buffer A for 5 min at a flow rate of 1 ml/min before re-equilibration in the initial solvent system. In order to determine the glycan structures, eluted glycans from individual samples were collected manually according to retention time, concentrated in a speed vacuum, and finally pooled into ALS and control samples. Likewise, eluted glycans from 19 ALS patients and 24 healthy control samples were numbered according to retention time and their amounts were calculated by Empower software (Waters). Glycans were assigned glucose unit (GU) values, and their structures were predicted by comparison to a glycan database made available for use in this analysis.

Exoglycosidase digestions: Exoglycosidase digestion was used to define the structures of glycans present in the pooled and the individual samples, in conjunction with HPLC. A series of exoglycosidases supplied by Prozyme (San Leandro, Calif.) was applied to the 2-AB-labeled N-glycans to remove their terminal sugar residues. The digestions were conducted using 50 mM sodium acetate buffer, pH 5.5, for 16 h at 37° C., at the following concentrations: 1 U/ml Arthobacter ureafaciens sialidase (ABS); 1 U/ml bovine testis β-galactosidase (BTG); 120 U/ml *Streptococcus pneumonia* β-hexoaminidase (SPH); 100 U/ml bovine kidney fucosidase (BKF); and 100 mU/ml jack bean α-mannosidase.

IgG purification: Serum IgG from ALS, inflammatory bowel disease, and multiple sclerosis patients, as well as from healthy controls were purified using protein G sepharose beads according to the manufacturer's instructions (GE healthcare, Germany). Briefly, 1 volume of serum (50 µl) was diluted with 1 volume of binding buffer (20 mM sodium phosphate, pH 7.0) and applied onto a protein G column. After 1 h of incubation at room temperature under rotating conditions, the beads were washed, the IgG fraction was eluted with 100 µl of elution buffer (0.1 M glycine-HCl, pH 2.7), and the supernatants were collected into 1 M Tris-HCl, pH 8.5, to neutralize the IgG solutions to pH 7.5. IgG concentration was determined by Bradford assay (Bio-Rad, Hercules, Calif.). IgG molecules were purified from individual serum samples (total of 71 samples), or from pool samples; a typical pool sample consisted of a balanced-serum mixture of 4 individuals.

Digestion of IgG Fc N-glycans: IgG molecules were reduced in Laemmli sample buffer (Bio-Rad) and 50 mM DTT for 10 min at 70° C., following by loading on one dimensional SDS-PAGE gels (10%). The gels were run in a MiniProtean3 device (Bio-Rad) for 75 min at 140-170 mV, at a current lower than 350 mA (18). The IgG molecules were visualized with Coomassie blue stain and the relevant bands were excised, cut into small pieces and dried using vacuum centrifugation. In accordance with previous procedure (Küster, B., et. al., ibid), three units of PNGase F diluted in 27 □l of 20 mM $NaHCO_3$, were added per 15 $mm^3$ of gel and incubated for 16 h at 37° C. N-glycans were extracted from the gel pieces by collecting the supernatants of sequential gel incubations with 3×200 µl double distilled water (DDW), 200 □l acetonitrile (ACN), 200 □l DDW and finally 200 □l ACN in a sonicating water bath for 30 min at room temperature. The collected supernatants were concentrated to a volume of 500 □l and then decontaminated using AG-50 ($H^+$ activated) ion-exchange resin. The glycans were dried for fluorescent labeling and HPLC analysis.

N-glycan analysis by matrix-assisted laser desorption ionization time-of-flight mass spectrometry (MALDI-TOF MS): HPLC-eluted glycans were collected according to retention time, concentrated in a speed vacuum and finally pooled into ALS and control samples. The samples were diluted in 1 □l DDW, desalted on a nafion membrane at room temperature for 30 min and mixed with equal volumes of saturated 2,5-dihydroxy benzoic acid (DHB) solution (Bruker Daltonics, Bremen, Germany), 50% ACN and 50% trifluoroacetic acid (TFA). The mixtures were analyzed by MALDI-TOF MS (Bruker Daltonics). A peptide calibration standard (Bruker Daltonics) was used to calibrate all spectra.

Removing N297 glycans from IgG: IgG $N^{297}$ glycans were removed by loading 50 µl of serum pooled from ALS patients onto protein G sepharose beads for 1 h at room temperature, with slow rotation. The beads were washed with glycan digestion buffer containing 0.01 M $NH_4HCO_3$, pH 8.5, followed by incubation with 0.5 U PNGase-F for 16 h at 37° C., under rotation conditions. The supernatant containing the digested glycans was removed and the N-glycan-free IgG molecules (deglycosylated IgG or PNGase F-treated IgG) were collected after elution and neutralization, as described above. The digestion was confirmed by one dimensional SDS-PAGE gels (10%) and immunoblot using *Erithrina cristagalli* lectin (ECL, Vector, Burlingame, Calif.), as previously described (Avidan, A., et. al. 2009. Glycoconj. J. 26, 1181-1195).

Cell cultures: The human SHSy5y neuroblastoma (CRL2266, ATCC, Manassas, Va.), HeLa (CL-2, ATCC) and PANC1 (CRL1469, ATCC) cell lines were grown in Dulbecco's modified Eagle's medium (DMEM) supplemented with 10% (v/v) fetal calf serum (FCS), 100 units/ml penicillin, 0.1 mg/ml streptomycin, and 2 mM L-glutamine, in a humidified 5% $CO_2$ atmosphere at 37° C.

The murine BW thymoma cell line, CD16-stable transfectants of BW cells (19), and the THP1 cell line (TIB-202, ATCC) were cultured in complete Roswell Park memorial Institute medium (RPMI-1640) supplemented with 10% (v/v) heat inactivated FCS, 100 units/ml penicillin, 0.1 mg/ml streptomycin, and 2 mM L-glutamine in a humidified 5% $CO_2$ atmosphere at 37° C. All medium ingredients were purchased from Invitrogen (Invitrogen, Carlsbad, Calif.).

Isolation of PBMCs and enriched peripheral NK cells: Human primary peripheral blood mononuclear cells (PBMCs) were purified from whole blood of healthy donors using Ficoll-Paque PLUS (GE Healthcare) according to the manufacturer's instructions. For isolation of a NK cell subset, PBMCs were purified from buffy coat extractions from healthy donors. NK cell subsets were purified by negative selection using antibody-coated magnetic bead separation (Invitrogen), following the manufacturer's instructions. Cell subset purity was assessed by flow cytometry, and determined to be 90%. The PBMCs or NK cells used as effector cells were activated by culturing in 10% heat inactivated FCS in RPMI-1640 containing 10 U/ml of IL-2 (eBiosciences, San Diego, Calif.) overnight.

Flow cytometry: To determine IgG affinity to SHSy5y cells, $1 \times 10^5$ cells were harvested and blocked with FACS buffer (2% FCS and 0.05% sodium azide in PBS, pH 7.5) (Biolegend, San Diego, Calif.). Subsequently, the cells were incubated with pools of serum samples or protein G-enriched IgG of ALS, inflammatory bowel disease, multiple sclerosis patients or healthy controls at a dilution of 1:10. Goat anti-human IgG allophycocyanin-conjugated F(ab')$_2$ (Jackson Immuno-Research, West Grove, Pa.) was used as a second step reagent. Propidium iodide (PI) was used to stain dead cells. For blocking CD16 on BPMCs, $1 \times 10^5$ cells were incubated in FACS buffer and purified anti-human CD16 antibodies (Biolegend). Subsequently, the cells were washed and incubated with pools of serum samples of ALS patients. Goat anti-human IgG conjugated with allophycocyanin (Jackson Immuno-Research) was used as a second step reagent. Flow cytometry was performed using a FACSCalibur flow cytometer (BD Biosciences, San Jose, Calif.), and fluorescence data were acquired using logarithmic amplification. Data files were acquired and analyzed using BD CellQuest 3.3 software.

Measurement of secreted cytokines: U-shape plates of 96 wells were incubated with serum, protein-G-enriched IgG or serum-depleted IgG samples for 3 h in a humidified 5% $CO_2$ atmosphere at 37° C. After IgG absorption, the plates were intensively washed and incubated with $1 \times 10^5$ healthy donor-enriched NK cells or CD16-transfected and control BW cells for 18 h in a humidified 5% $CO_2$ atmosphere at 37° C. The media were collected and levels of secreted human IFN☐ and mouse interleukin IL-2 were assessed using a commercial ELISA kit (Biolegend), according to the manufacturer's instructions and as described (Hershkovitz, O., et. al. (2009). J. Immunol. 183, 2610-2621).

ADCC assay: Antibody-dependent cytolytic activity was evaluated in co-cultures of neuroblastoma cells with serum or purified IgG from the different samples and PBMCs in a 4 h CFSE/7-AAD flow cytometry assay, as previously described (Cohen, M., et. al. (2010). Sialylation of 3-methylcholanthrene-induced fibrosarcoma determines antitumor immune responses during immunoediting. J. Immunol. 185, 5869-5878). Neuroblastoma cells, serving as target cells, were pre-incubated with diluted sera (1:10) or with purified ALS-IgG before and after removing $N^{297}$ glycans, for 1 h on ice. The cells were washed in RPMI medium and plated at a density of $5 \times 10^4$ cells per well of a 96-well plate. The isolated PBMCs were pre-labeled with CFSE (Invitrogen) and co-cultured with the complex IgG-target cells at effector/target (E/T) cell ratios of 10:1, in a final volume of 200 µl RPMI medium at 37° C. for 4 h in a humidified $CO_2$ incubator. To measure spontaneous lysis, target cell cultures were used. For cytolytic activity independent of IgG, target cells were co-cultured with PBMCs. For measuring lysis of target cells by IgG, target cells were incubated with IgG or serum samples. To confirm that the ADCC response occurred via NK cells, the PBMCs were pre-treated with anti-CD16 antibodies (BD Biosciences) for 30 min on ice and then co-cultured with target cells before coupling with the IgG. Killing assays were performed in quadruplicate. Acquisition was performed immediately afterwards on a FACScan flow cytometer equipped with a single 488 nm Argon laser. CFSE fluorescence and 7-AAD emission were detected in the FL-1 and FL-3 channels, respectively. Analysis was performed with FlowJo software (Three Star, Ashland, Oreg.).

G93A-SOD1 mice and frozen sections: Frozen sections of brain and spinal cord tissues of SOD1G93A transgenic and wild-type mice were donated by Professor Daniel Offen from Rabin Medical Center-Beilinson Campus, The Sackler School of Medicine at Tel-Aviv University. The G93A-SOD1 transgenic mice were purchased from The Jackson Laboratory and were bred and maintained in the Animal Breeding Center of the Tel-Aviv University. All experiments and procedures were approved by the Animal Care and Use Committee of Tel-Aviv University.

For this experiment, three SOD1G93A transgenic mice, 130 days old (the end-stage of the disease) (21) and 3 wild-type age-matched littermates were deeply anesthetized, decapitated, and perfused with isotonic saline followed by 4% paraformaldehyde via cardiac puncture. Brain and spinal cord organs were immediately equilibrated in a 30% sucrose solution for 24 h, embedded in a frozen tissue matrix (Tissue-Tek OCT, Torrance, Calif.), cryosectioned and stored at −80° C. until section staining took place.

Immunohistochemistry: Tick slides of 8 µm were blocked in PBS containing 1% BSA for 1 h and stained with mouse anti-neuronal nuclear protein (NeuN; 1:25, GeneTex, Irvine, Calif.), mouse anti-CD16 (ASH 1975; 1:50, Santa-Cruz Biotechnologies, Santa Cruz, Calif.), rabbit anti-ionized calcium binding adaptor molecule 1 (Iba-1; 1:1000, Chemicon, Billerica, Mass.) antibodies, protein-G-purified ALS-IgG treated or untreated with PNGase F, and healthy volunteer IgG, at concentrations of 16 µg/ml. Anti-mouse CY5-, anti-rabbit CY3-, anti-human FITC-tagged or anti-mouse dyelight 549 secondary antibodies with low cross reactivity to other species (Jackson Immuno-Research), were used for cell visualization. For preserving fluorescence and for nuclei detection, a drop of VECTASHIELD mounting medium with DAPI was added (Vector). The sections were examined under Zeiss Laser Scanning Confocal Microscope, with magnification x60. The percentage of co-expression/localization was calculated by measuring the ratio between two crossed intensities in a defined area using Olympus Fluoview FV1000 version 2b.

Statistical analysis: For measuring the amounts of total N-glycans in serum and for determining the IgG glycan structures and their amounts, individual serum samples of each group were used. The data shown correspond to pooled or single representative experiments, as indicated, and are expressed as mean values±SEM. Significant differences in results were determined using three paired Student's t-tests, the Mann-Whitney test, the Welch t-test, and t-test assuming equal variances, with p<0.05 in the triplet tests being considered as significant. The p values observed for N-glycans was calculated before multiple testing. The p values after multiple testing differed insignificantly compared to the values before. All statistical analyses were performed at the Bioinformatics Core Facility at Ben-Gurion University using Partek® Genomics Suite™ software.

The in vitro experiments were repeated at least 3 times with similar patterns of responses. The data shown correspond to pooled or single representative experiments, as indicated; and are expressed as mean values±SD. Significant differences in results were determined using the two-sided Student's t-test, with a p<0.05 being considered as significant.

Example 1

Glycome Analysis Yields Specific N-Glycan Expression Patterns in Human Subjects

Since blood substances are present in the cerebrospinal fluid, it was of interest to determine whether the serum substance repertoire of ALS patients might contain uncommon glycoforms. Accordingly, the total N-glycans derived from serum samples of ALS patients and healthy volunteers were sequenced. Whole serum N-glycans from 19 patients were fractionated by quantitative NP-HPLC, according to glucose units (GU). The thirteen fractions observed were numbered (FIG. 1) and each was pooled and subsequently digested by exoglycosidases, with structural assignments being made using database-matching, combined with MALDI-TOF MS. The results from the pooled fractions were compared to those of control samples pooled from fractionated N-glycans of 24 healthy volunteer sera. The results revealed similar number of fractions and glycan structures in both patient and healthy serum samples. Most of the fractions contained 3-5 glycan structures in each fraction, namely bi- or tri-antennary high mannose and complex type structures (Table 1).

TABLE 1

Profiles of total N-Glycans derived from pooled sera of ALS patients.
Profiles were observed for both pooled or individual sera of ALS patients and healthy control candidates by using normal phase HPLC and MALDI-TOF MS methods.

| HPLC Peak no. | GU | Assignment | Undigestion | ABS | ABS BTG | ABS BTG SPH | ABS BTG SPH BKF | BTG | BTG SPH | BTG SPH BKF | SPH | SPH BKF | MALDI TOF MS Molec. mass detected |
|---|---|---|---|---|---|---|---|---|---|---|---|---|---|
| 1 | 4.39 | M3 | — | — | — | — | — | — | — | — | 100 | 100 | |
|  | 5.39 | A2 | 100 | — | — | — | — | — | — | — | — | — | 1460.8 |
| 2 | 4.39 | M3 | — | — | — | — | — | — | — | — | — | 100 | |
|  | 4.86 | Fc(6) | — | — | — | — | — | — | — | — | 100 | — | |
|  | 5.87 | Fc(6)A2 | 100 | — | — | — | — | — | — | — | — | — | 1605.9 |
| 4 | 4.36 | M3 | — | — | — | — | — | — | — | 86 | — | — | |
|  | 5.31 | M4 | — | — | — | — | — | — | — | 4 | — | — | |
|  | 5.77 | A2B | — | — | — | — | — | — | — | 10 | — | — | |
|  | 4.83 | Fc(6) | — | — | — | — | — | — | 86 | — | — | — | |
|  | 5.79 | Fc(6)M4 | — | — | — | — | — | — | 4 | — | — | — | |
|  | 6.2 | Fc(6)A2B | — | — | — | — | — | 10 | 10 | — | — | — | |
|  |  | Fc(6)M4A1 | — | — | — | — | — | 4 | — | — | — | — | |
|  | 5.8 | Fc(6)A2 | — | — | — | — | — | 86 | — | — | — | — | |
|  | 6.65 | Fc(6)A2G1 | 86 | — | — | — | — | — | — | — | — | — | 1767.9 |
|  | 6.87 | Fc(6)A2BG1 | 10 | — | — | — | — | — | — | — | — | — | 1971.1 |
|  | 6.99 | Fc(6)M4A1G1 | 4 | — | — | — | — | — | — | — | — | — | 1565.7 |
| 5 | 4.39 | M3 | — | — | — | — | — | — | 83 | 78.7 | — | — | |
|  | 6.91 | M6, D2 | — | — | — | — | — | — | 17 | 21.3 | — | — | |
|  | 5.43 | A2 | — | — | — | — | — | 58.2 | — | — | — | — | |
|  | 7.31 | M6A1 | 27.6 | — | — | — | — | 41.8 | — | — | — | — | ND |
|  | 7.17 | A2G2 | 72.4 | — | — | — | — | — | — | — | — | — | 1784.1 |
| 6 | 4.37 | M3 | — | — | — | — | — | — | — | 86.75 | — | — | |
|  | 5.77 | A2B | — | — | — | — | — | — | — | 8.74 | — | — | |
|  | 6.9 | M6, D2 | — | — | — | — | — | — | — | 4.51 | — | — | |
|  | 4.83 | Fc(6) | — | — | — | — | — | — | 88.41 | — | — | — | |
|  | 6.18 | Fc(6)A2B | — | — | — | — | — | — | 9.24 | — | — | — | |
|  | 7.31 | Fc(6)M6, D2 | — | — | — | — | — | — | 2.36 | — | — | — | |
|  | 5.81 | Fc(6)A2 | — | — | — | — | — | 80.32 | — | — | — | — | |
|  | 6.13 | Fc(6)A2B | — | — | — | — | — | 8.45 | — | — | — | — | |
|  | 7.64 | Fc(6)M6A1 | — | — | — | — | — | 11.23 | — | — | — | — | |
|  | 7.59 | Fc(6)A2G2 | 80.32 | — | — | — | — | — | — | — | — | — | 1930.3 |
|  | 7.71 | Fc(6)A2BG2 | 8.45 | — | — | — | — | — | — | — | — | — | 2133.5 |
|  |  | Fc(6)M6A1 | 11.23 | — | — | — | — | — | — | — | — | — | 1890.2 |
| 7 | 4.37 | M3 | — | — | — | — | 92.11 | — | — | — | — | — | |
|  | 5.74 | A2B | — | — | — | — | 1.92 | — | — | — | — | — | |
|  | 7.94 | M7 | — | — | 5.27 | — | 5.97 | — | — | — | — | — | |
|  | 4.83 | (Fc(6 | — | — | — | — | — | — | — | — | — | — | |
|  | 6.21 | Fc(6)A2B | — | — | 1.58 | — | — | — | — | — | — | — | |
|  | 5.45 | A2 | — | — | 86.02 | — | — | — | — | — | — | — | |
|  | 5.88 | Fc(6)A2 | — | — | 7.13 | — | — | — | — | — | — | — | |
|  | 7.18 | A2G2 | — | 81.66 | — | — | — | — | — | — | — | — | |
|  | 7.6 | Fc(6)A2G2 | — | 8.31 | — | — | — | — | — | — | — | — | |
|  |  | Fc(6)A2G2S1 | 8.31 | — | — | — | — | — | — | — | — | — | ND |

TABLE 1-continued

Profiles of total N-Glycans derived from pooled sera of ALS patients.
Profiles were observed for both pooled or individual sera of ALS patients and healthy
control candidates by using normal phase HPLC and MALDI-TOF MS methods.

| HPLC Peak no. | GU | Assignment | Undigestion | ABS | ABS BTG | ABS BTG SPH | ABS BTG SPH BKF | BTG | BTG SPH | BTG SPH BKF | SPH | SPH BKF | MALDI TOF MS Molec. mass detected |
|---|---|---|---|---|---|---|---|---|---|---|---|---|---|
| | 8.01 | Fc(6)A2BG2S1 | 1.82 | 1.82 | — | — | — | — | — | — | — | — | ND |
| | | M7 | 8.21 | 8.21 | — | — | — | — | — | — | — | — | 1701.8 |
| | | A2G2S1 | 81.66 | — | — | — | — | — | — | — | — | — | 1784.0 (NS) |
| 8 | 5.88 | M3 | — | — | — | 25.42 | 93.05 | — | — | — | — | — | |
| | 7.18 | M3B | — | — | — | — | 1.39 | — | — | — | — | — | |
| | 7.6 | A2B | — | — | — | — | 2.41 | — | — | — | — | — | |
| | 7.92 | M7 | — | — | — | — | 3.15 | — | — | — | — | — | |
| | 4.86 | Fc(6) | — | — | — | 72.18 | — | — | — | — | — | — | |
| | 6.23 | Fc(6)A2B | — | — | 2.59 | 2.4 | — | — | — | — | — | — | |
| | 5.44 | A2 | — | — | 24.74 | — | — | — | — | — | — | — | |
| | 5.87 | Fc(6)A2 | — | — | 72.66 | — | — | — | — | — | — | — | |
| | 7.17 | A2G2 | — | 23.28 | | | | | | | | | |
| | | Fc(6)A2BG1 | — | 2.59 | — | — | — | — | — | — | — | — | |
| | 7.59 | Fc(6)A2G2 | — | 74.13 | — | — | — | — | — | — | — | — | |
| | | Fc(6)A2BG1S1 | 2.59 | — | — | — | — | — | — | — | — | — | 1929.9 (NS) |
| | 8.33 | A2G2S1 | 23.28 | — | — | — | — | — | — | — | — | — | 1783.9 (NS) |
| | | Fc(6)A2G2S1 | 74.13 | — | — | — | — | — | — | — | — | — | ND |
| 9 | 4.38 | M3 | — | — | — | 95.15 | 96.31 | — | — | — | — | — | |
| | 5.75 | A2B | — | — | — | — | 1.51 | — | — | — | — | — | |
| | 6.6 | A1F1G1 | — | — | — | 0.47 | 0.35 | — | — | — | — | — | |
| | 8.88 | M8 | — | 1.01 | 0.7 | 0.8 | 1.83 | — | — | — | — | — | |
| | 4.86 | Fc(6) | — | — | — | 1.78 | — | — | — | — | — | — | |
| | 6.21 | Fc(6)A2B | — | — | 2.3 | 1.8 | — | — | — | — | — | — | |
| | 7.03 | A2F1G1 | — | — | 0.7 | — | — | — | — | — | — | — | |
| | 5.43 | A2 | — | — | 94.08 | — | — | — | — | — | — | — | |
| | 5.86 | Fc(6)A2 | — | — | 1.63 | — | — | — | — | — | — | — | |
| | 7.15 | A2G2 | — | 94.57 | — | — | — | — | — | — | — | — | |
| | 7.69 | Fc(6)A2G2 | — | 1.42 | — | — | — | — | — | — | — | — | |
| | 7.96 | Fc(6)A2BG2 | — | 2.29 | — | — | — | — | — | — | — | — | |
| | 7.96 | A2F1G2 | — | 0.71 | — | — | — | — | — | — | — | — | |
| | | A2F1G2S1 | 0.71 | — | — | — | — | — | — | — | — | — | ND |
| | | M8 | 1 | — | — | — | — | — | — | — | — | — | 1863.8 |
| | 8.74 | Fc(6)A2G2S1 | 1.42 | — | — | — | — | — | — | — | — | — | ND |
| | | Fc(6)A2BG2S1 | 2.29 | — | — | — | — | — | — | — | — | — | 2132.2 (NS) |
| | | A2G2S2 | 94.57 | — | — | — | — | — | — | — | — | — | 1783.8 (NS) |
| 10 | 4.38 | M3 | — | — | — | 11.82 | 65.3 | — | — | — | — | — | |
| | 5.32 | A1B | — | — | — | — | 3.75 | — | — | — | — | — | |
| | 5.79 | A2B | — | — | — | 1.75 | 25.58 | — | — | — | — | — | |
| | 6.62 | A1F1G1 | — | — | — | 4.94 | 5.37 | — | — | — | — | — | |
| | 4.85 | Fc(6) | — | — | — | 52.81 | — | — | — | — | — | — | |
| | 6.21 | Fc(6)A2B | — | — | — | 28.67 | — | — | — | — | — | — | |
| | 5.57 | A2 | — | — | 7.91 | — | — | — | — | — | — | — | |
| | 6.21 | Fc(6)A2B | — | — | 33.1 | — | — | — | — | — | — | — | |
| | 5.88 | Fc(6)A2 | — | — | 49.25 | — | — | — | — | — | — | — | |
| | | A3 | — | — | 3.9 | — | — | — | — | — | — | — | |
| | 7.09 | A2F1G1 | — | — | 5.84 | — | — | — | — | — | — | — | |
| | 7.34 | A2G2 | — | 8.74 | — | — | — | — | — | — | — | — | |
| | 7.6 | Fc(6)A2G2 | — | 43.74 | — | — | — | — | — | — | — | — | |
| | 7.73 | Fc(6)A2BG2 | — | 33.15 | — | — | — | — | — | — | — | — | |
| | 8.01 | A2F1G2 | — | 6.47 | — | — | — | — | — | — | — | — | |
| | 8.43 | A3G3 | — | 7.9 | — | — | — | — | — | — | — | — | |
| | 8.94 | A2G2S2 | 7 | — | — | — | — | — | — | — | — | — | 1784.7 (NS) |
| | 9.11 | Fc(6)A2G2S2 | 48 | — | — | — | — | — | — | — | — | — | 1929.8 (NS) |
| | | Fc(6)A2BG2S2 | 28.67 | — | — | — | — | — | — | — | — | — | ND |
| | 9.17 | A2F1G2S1 | 6.47 | — | — | — | — | — | — | — | — | — | 1929.8 (NS) |
| | | A3G3S1 | 7.81 | — | — | — | — | — | — | — | — | — | ND |

TABLE 1-continued

Profiles of total N-Glycans derived from pooled sera of ALS patients.
Profiles were observed for both pooled or individual sera of ALS patients and healthy
control candidates by using normal phase HPLC and MALDI-TOF MS methods.

| HPLC Peak no. | GU | Assignment | Undigestion | ABS | ABS BTG | ABS BTG SPH | ABS BTG SPH BKF | BTG | BTG SPH | BTG SPH BKF | SPH | SPH BKF | MALDI TOF MS Molec. mass detected |
|---|---|---|---|---|---|---|---|---|---|---|---|---|---|
| 11 | 4.38 | M3 | — | — | — | 53.03 | 72.9 | — | — | — | — | — | |
| | 8.62 | M8 D2 D3 | — | 13 | 13 | 8.38 | 13.18 | — | — | — | — | — | |
| | 9.52 | M9 | 7.53 | 7.53 | 12.14 | — | 14.34 | — | — | — | — | — | 2025.7 |
| | 4.85 | Fc(6) | — | — | — | 38.58 | — | — | — | — | — | — | |
| | | Fc(6)A2 | — | — | 24.18 | — | — | — | — | — | — | — | |
| | 5.87 | A3 | — | — | 33.39 | — | — | — | — | — | — | — | |
| | 6.12 | A3B | — | 2.19 | 10.53 | — | — | — | — | — | — | — | |
| | 6.53 | A4 | — | — | 4.08 | — | — | — | — | — | — | — | |
| | 6.95 | Fc(6)A4 | — | — | 2.58 | — | — | — | — | — | — | — | |
| | 6.92 | A3BG1 | — | 2.19 | — | — | — | — | — | — | — | — | |
| | 7.8 | A3BG2 | — | 5.92 | — | — | — | — | — | — | — | — | |
| | | A3G3 | — | 13.12 | — | — | — | — | — | — | — | — | |
| | 8.39 | A3BG3 | — | 23.32 | — | — | — | — | — | — | — | — | |
| | 8.97 | A4G3 | — | 14.96 | — | — | — | — | — | — | — | — | |
| | | A3B3S1 | 23.32 | — | — | — | — | — | — | — | — | — | ND |
| | | A3G3S1 | 13.12 | — | — | — | — | — | — | — | — | — | ND |
| | 9.53 | M8S1 | 30.77 | — | — | — | — | — | — | — | — | — | ND |
| | | A4G3S1 | 14.96 | — | — | — | — | — | — | — | — | — | ND |
| 12 | 4.38 | M3 | — | — | — | 89.81 | 90.26 | — | — | — | — | — | |
| | 4.72 | Fc(6) | — | — | — | 5.13 | 4.73 | — | — | — | — | — | |
| | 6.65 | A1F1G1 | — | — | — | 5.06 | 5.01 | — | — | — | — | — | |
| | 5.86 | A3 | — | — | 84.34 | — | — | — | — | — | — | — | |
| | 6.24 | Fc(6)A3 | — | — | 6.8 | — | — | — | — | — | — | — | |
| | 6.49 | A4 | — | — | 2.55 | — | — | — | — | — | — | — | |
| | 7.45 | A3F1G1 | — | — | 6.31 | — | — | — | — | — | — | — | |
| | 8.35 | A3G3 | — | 85.11 | — | — | — | — | — | — | — | — | |
| | 8.71 | Fc(6)A3G3 | — | 6.39 | — | — | — | — | — | — | — | — | |
| | | A3F1G3 | — | 5.69 | — | — | — | — | — | — | — | — | |
| | 9.07 | A4G3 | — | 2.81 | — | — | — | — | — | — | — | — | |
| | 9.97 | A3G3S2 | 85.11 | — | — | — | — | — | — | — | — | — | 2148.6 (NS) |
| | | Fc(6)A3G3S1 | 6.39 | — | — | — | — | — | — | — | — | — | ND |
| | | A4G3S1 | 2.8 | — | — | — | — | — | — | — | — | — | ND |
| | 10.13 | A3F1G3S1 | 5.69 | — | — | — | — | — | — | — | — | — | ND |
| 13 | 4.34 | M3 | — | — | — | 34.78 | 58.14 | — | — | — | — | — | |
| | 6.58 | A1F1G1 | — | — | — | 54.14 | 41.86 | — | — | — | — | — | |
| | 4.84 | Fc(6) | — | — | — | 8.6 | — | — | — | — | — | — | |
| | 7.06 | Fc(6)A1F1G1 | — | — | — | 2.48 | — | — | — | — | — | — | |
| | 5.85 | A3 | — | — | 26.49 | — | — | — | — | — | — | — | |
| | 6.25 | A4 | — | — | 6.31 | — | — | — | — | — | — | — | |
| | 6.49 | Fc(6)A3 | — | — | 6.24 | — | — | — | — | — | — | — | |
| | 7.5 | A3F1G1 | — | — | 52.56 | — | — | — | — | — | — | — | |
| | 7.89 | Fc(6)A3F1G2 | — | — | 4.75 | — | — | — | — | — | — | — | |
| | 8.29 | A3G3 | — | 27.19 | — | — | — | — | — | — | — | — | |
| | 8.67 | A4G3 | — | 8 | — | — | — | — | — | — | — | — | |
| | | A3F1G3 | — | 52.7 | — | — | — | — | — | — | — | — | |
| | 8.99 | Fc(6)A3G3 | — | 5.85 | — | — | — | — | — | — | — | — | |
| | 5.54 | Fc(6)A3F1G3 | — | 6.24 | — | — | — | — | — | — | — | — | |
| | | A3G3S3 | 27.19 | — | — | — | — | — | — | — | — | — | ND |
| | | A4G3S2 | 8 | — | — | — | — | — | — | — | — | — | ND |
| | 10.46 | A3F1G3S2 | 52.7 | — | — | — | — | — | — | — | — | — | ND |
| | | Fc(6)A3G3S2 | 5.85 | — | — | — | — | — | — | — | — | — | ND |
| | | Fc(6)A3F1G3S1 | 6.24 | — | — | — | — | — | — | — | — | — | ND |

The complex structures were composed of neutral and multi-sialylated glycans. Some of these were core fucosylated, while others bear bisecting N-acetyl glucosamine (GlcNAc) or sialyl-Le$^x$ epitopes. Despite the fact that many structures were found to be capped by sialic acid residues, separation by weak ion-exchange HPLC according to charge failed to provide full sequencing information due to partial glycan separation (data not shown). Thus, the glycans partially sequenced by NP-HPLC separation were next subjected to sample fractionation.

In addition to the full sequencing of serum glycans, N-glycan amounts from individual samples were calculated by dividing areas under specific peaks to total peak area measured in each HPLC spectrum. Following paired Student's t-test analysis of the individual samples, 4 fractions met statistical criteria ($P<0.05$) and were selected as candidate disease glycans (Table 2).

TABLE 2

Statistic analyses comparing N-glycans derived from 19 ALS patient sera and from 24 healthy candidate sera

| HPLC Peak no. | Structure | Assignment | ANOVA | Mann-Whitney | Welch T-test | Fold Change |
|---|---|---|---|---|---|---|
| 1 | 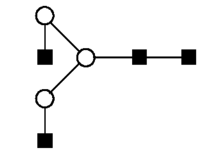 | A2 | 0.578 | 0.230 | 0.605 | −1.13 |
| 2 | 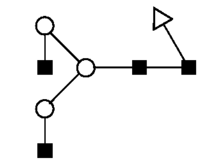 | Fc(6)A2 | 0.277 | 0.123 | 0.238 | −1.09 |
| 3 | 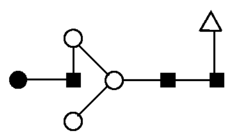 | Fc(6)A1G1 | 0.434 | 0.317 | 0.432 | −1.09 |
| 4 | 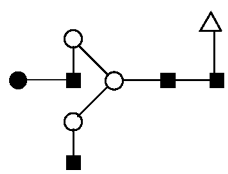 | Fc(6)A2G1 | 0.058 | 0.047 | 0.043 | −1.15 |
| | | Fc(6)A2BG1 | | | | |
| | | Fc(6)M4A1G1 | | | | |
| 5 | 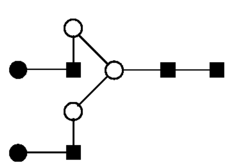 | A2G2 | 0.118 | 0.063 | 0.140 | +1.83 |
| | | M6A1 | | | | |

TABLE 2-continued

Statistic analyses comparing N-glycans derived from 19 ALS patient sera and from 24 healthy candidate sera

| HPLC Peak no. | Structure | Assignment | ANOVA | Mann-Whitney | Welch T-test | Fold Change |
|---|---|---|---|---|---|---|
| 6 | 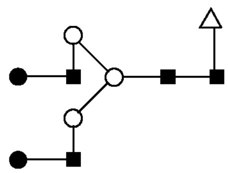 | Fc(6)A2G2 | 0.008 | 0.020 | 0.003 | −1.32 |
| | | Fc(6)A2BG2 | | | | |
| | | Fc(6)M6A1 | | | | |
| 7 | 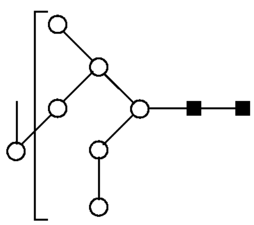 | M7 | 0.480 | 0.511 | 0.550 | +1.12 |
| | | A2G2S1 | | | | |
| | | Fc(6)A2G2S1 | | | | |
| | | Fc(6)A2BG2S1 | | | | |
| 8 | 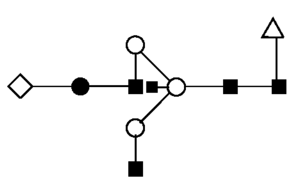 | Fc(6)A2BG1S1 | 0.012 | 0.014 | 0.009 | −1.16 |

TABLE 2-continued

Statistic analyses comparing N-glycans derived from 19 ALS patient sera and from 24 healthy candidate sera

| HPLC Peak no. | Structure | Assignment | ANOVA | Mann-Whitney | Welch T-test | Fold Change |
|---|---|---|---|---|---|---|
| | | A2G2S1 | | | | |
| | | Fc(6)A2G2S1 | | | | |
| 9 | 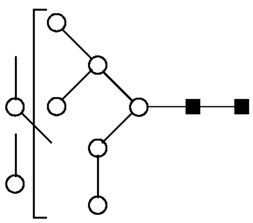 | M8 | 0.094 | 0.086 | 0.064 | +1.12 |
| | | Fc(6)A2G2S1 | | | | |
| | | Fc(6)A2BG2S1 | | | | |
| | | A2G2S2 | | | | |
| 10 | 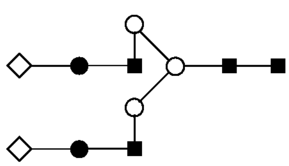 | A2G2S2 | 0.023 | 0.007 | 0.019 | +1.36 |
| | | Fc(6)A2G2S2 | | | | |

TABLE 2-continued

Statistic analyses comparing N-glycans derived from 19 ALS patient sera and from 24 healthy candidate sera

| HPLC Peak no. | Structure | Assignment | ANOVA | Mann-Whitney | Welch T-test | Fold Change |
|---|---|---|---|---|---|---|
| | | Fc(6)A2BG2S2 | | | | |
| | | A2F1G2S1 | | | | |
| | | A3G3S1 | | | | |
| 11 | 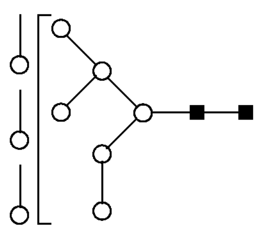 | M9 | 0.039 | 0.079 | 0.024 | −1.53 |
| | | A3G3S1 | | | | |
| | | A3BG3S1 | | | | |
| | | A4G3S1 | | | | |

TABLE 2-continued
Statistic analyses comparing N-glycans derived from 19 ALS patient sera and from 24 healthy candidate sera
| HPLC Peak no. | Structure | Assignment | ANOVA | Mann-Whitney | Welch T-test | Fold Change |
|---|---|---|---|---|---|---|
| 12 | 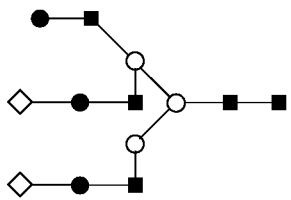 | A3G3S2 | 0.257 | 0.193 | 0.262 | −1.22 |
| | 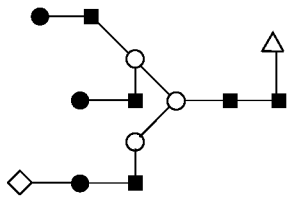 | Fc(6)A3G3S1 | | | | |
| | 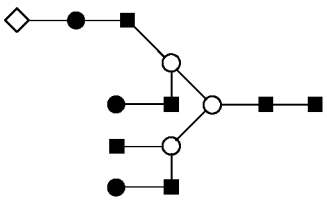 | A4G3S1 | | | | |
| | 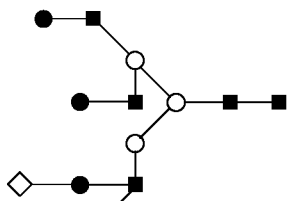 | A3F1G3S1 | | | | |
| 13 | 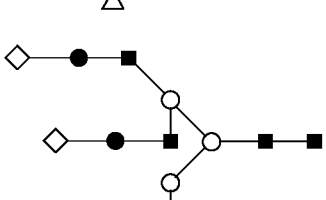 | A3G3S3 | 0.001 | 0.001 | 0.001 | +1.67 |
| | 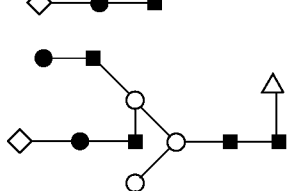 | Fc(6)A3G3S2 | | | | |
| | 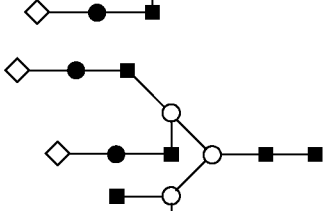 | A4G3S2 | | | | |

TABLE 2-continued

Statistic analyses comparing N-glycans derived from 19 ALS patient sera and from 24 healthy candidate sera

| HPLC Peak no. | Structure | Assignment | ANOVA | Mann-Whitney | Welch T-test | Fold Change |
|---|---|---|---|---|---|---|
| | [structure diagram] | A3F1G3S2 | | | | |
| | [structure diagram] | Fc(6)A3F1G3S1 | | | | |

◇ Sialic acid;
■ GlcNAc;
● Galactose;
△ Fucose;
○ Mannose
Fold of change:
(+) assigns that N-glycan amounts in ALS sera are higher relative to glycans from healthy candidate sera and
(−) assigns the contrary.

Two of the fractions, peaks 10 and 13, contained abundant bi- and tri-antennary glycans that included up to two sialic acid residues or sialyl-Le$^x$ epitopes. These structures were significantly up-regulated in ALS samples. The two other fractions, peaks 6 and 8, were rich in core fucosylation and galactosylation and were plentiful in healthy samples. The unique glycans detected upon individual sample analysis were correlated with glycan alterations found in the pooled samples. Thus, this pilot study indicates that glycans are potential candidate markers of ALS.

Figure 2:
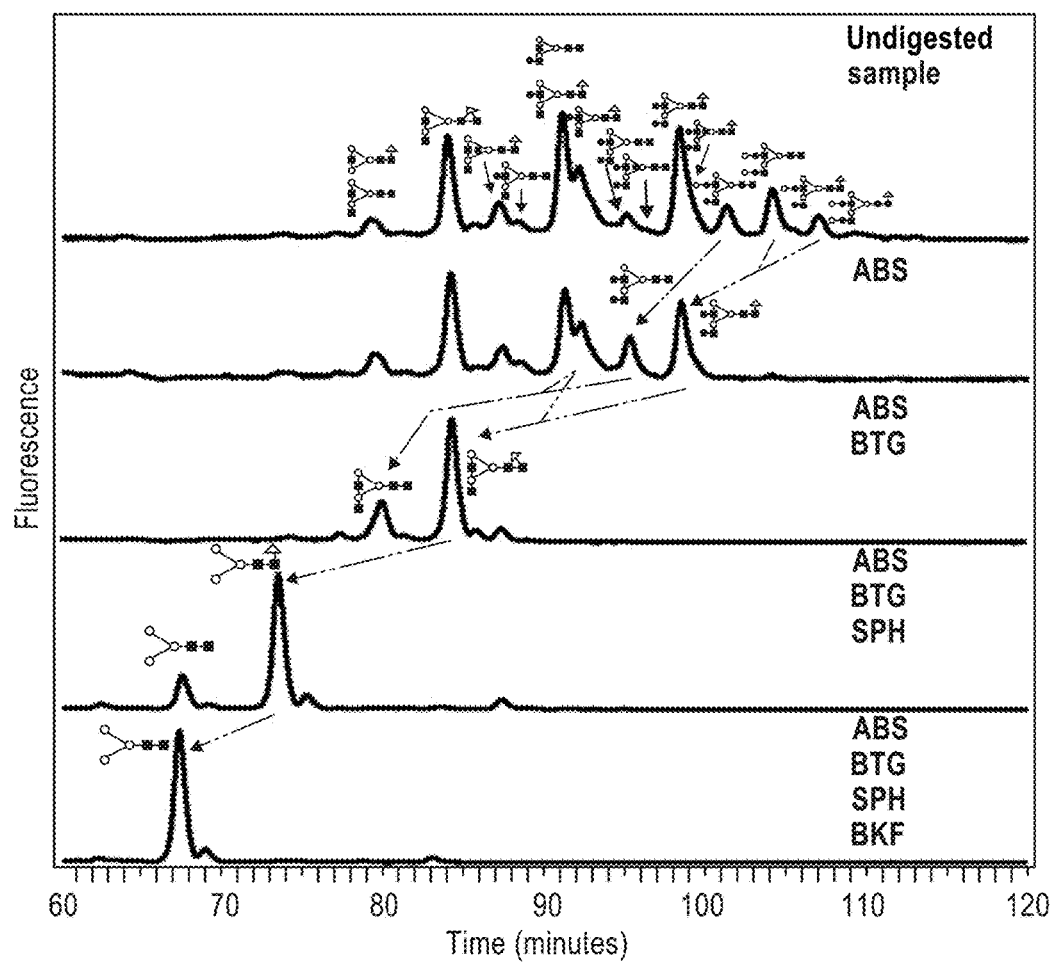
FIG. 2 Sequential exoglycosidase digestions of the pool of glycans released from normal human serum IgG and measured by normal phase HPLC. The IgG glycan pool from individual samples (undigested sample) was incubated sequentially with *Arthrobacter ureafaciens* sialidase (ABS), bovine testes β-galactosidase (BTG), Jack bean β-hexosaminidase (JBH) and *Charonia lampas* α-fucosidase (BKF). The figure panel shows the HPLC separation of normal IgG glycans and the glycan structure symbols.

The involvement of the IgG Fc domain in IgG uptake was suggested in an ALS animal model. Accordingly, IgG molecules were purified from individual serum samples of 19 ALS, 22 inflammatory bowel disease, and 6 multiple sclerosis patients, and from 24 healthy controls. N-glycans were released from a total of 71 individual samples and separately analyzed by NP-HPLC and MALDI-TOF MS. Results showed similar bi-antennary complex structures (FIG. 2 and Table 3).

TABLE 3

Profiles of $N^{297}$-Glycans derived from sera of ALS patients. Profiles were observed for individual sera of ALS, patients with inflammatory bowel disease, multiple sclerosis patients, and healthy control candidates by using normal phase HPLC and MALDI-TOF MS methods.

| | | | NP-HPLC | | | | | |
|---|---|---|---|---|---|---|---|---|
| | | | Exoglycosidase added NP-HPLC % Area | | | | | |
| Peak no. | GU | Assignment | Undigestion | ABS | ABS BTG | ABS BTG SPH | ABS BTG SPH BKF | MALDI TOF MS Molec. Mass detected |
| | 4.39 | M3 | — | — | — | 16.71 | 87.14 | |
| | 4.51 | | — | — | — | 1.92 | 8.31 | |
| | 4.87 | Fc(6) | — | — | — | 68.1 | — | |
| | 5.02 | | — | — | — | 6.69 | — | |
| | 4.94 | A1 | 0.56 | 1.41 | 2.03 | — | — | |
| | 5.33 | A1B | 0.85 | 0.93 | 2.7 | — | 0.9 | |
| 1 | 5.47 | A2 | 3.32 | 6.38 | 23.57 | — | — | ND |
| | | Fc(6)A1 | | | | — | — | |
| | 5.6 | | 0.97 | 1.03 | 2.58 | — | — | |
| | 5.77 | A2B | — | — | 0.9 | 0.87 | 3.64 | |
| | 5.81 | Fc(6)A1B | — | — | — | 0.9 | — | |

TABLE 3-continued

Profiles of $N^{297}$-Glycans derived from sera of ALS patients. Profiles were observed for individual sera of ALS, patients with inflammatory bowel disease, multiple sclerosis patients, and healthy control candidates by using normal phase HPLC and MALDI-TOF MS methods.

| | | | NP-HPLC | | | | | |
|---|---|---|---|---|---|---|---|---|
| | | | | | Exoglycosidase added NP-HPLC % Area | | | |
| Peak no. | GU | Assignment | Undigestion | ABS | ABS BTG | ABS BTG SPH | ABS BTG SPH BKF | MALDI TOF MS Molec. Mass detected |
| 2 | 5.9 | Fc(6)A2 | 13.18 | 21.7 | 60.85 | — | — | 1605.7 |
| | | | 2.1 | 1.88 | 3.4 | — | — | |
| 3 | 6.23 | Fc(6)A2B | 5.1 | 6.15 | 4.85 | 5.61 | — | 1810.3 |
| 4 | 6.39 | A2G1 | 2.4 | 2.06 | — | — | — | 16621.1 |
| 5 | 6.67/6.7 | Fc(6)A2G1 | 27.5 | 27.38 | — | — | — | 1768.5 |
| | | Fc(6)A2BG1 | 1.5 | 1.5 | — | — | — | 1972.8 |
| | | A2BG1 | 2 | 2 | — | — | — | 1825.8 |
| 6 | 7.16 | A2G2 | 3.84 | 8.43 | — | — | — | 1784.6 |
| 7 | 7.33 | A2BG2 | 0.8 | 0.9 | — | — | — | ND |
| 8 | 7.58 | Fc(6)A2G2 | 16.8 | 16.73 | — | — | — | 1931.8 |
| 9 | 7.65 | Fc(6)A2BG2 | 2.23 | 1.5 | — | — | — | 2134.3 |
| 10 | 7.91 | A2G2S1 | 5.33 | — | — | — | — | 1784.49 (NS) |
| 11 | 8.31 | Fc(6)A2G2S1 | 7.02 | — | — | — | — | 2220 |
| | 8.47 | | 1.2 | — | | | | |
| 12 | 8.74 | A2G2S2 | 3.26 | — | — | — | — | ND |
| 13 | 9.1 | Fc(6)A2G2S2 | 1.5 | — | — | — | — | ND |

Paired Student's t-test analyses of glycan amounts in ALS and healthy subjects revealed two structures in amounts that met our statistical criteria as being unique $N^{297}$ glycans (Table 4).

TABLE 4

Statistic analyses comparing $N^{297}$-glycans digested from serum IgG of 19 ALS patients and of 24 healthy candidates.

| | | | ALS Vs. Healthy control | | | |
|---|---|---|---|---|---|---|
| | | | p-Value | | | |
| Peak no. | Structure | Assignment | ANOVA | Mann-Whitney | Welch T-test | Fold Change |
| 1 | | A2 | 0.9 | 0.693 | 0.9 | −1.03 |
| | | Fc(6)A1 | | | | |
| 2 | | Fc(6)A2 | 0.906 | 0.717 | 0.906 | −1.02 |

TABLE 4-continued

Statistic analyses comparing $N^{297}$-glycans digested from serum IgG of 19 ALS patients and of 24 healthy candidates.

| Peak no. | Structure | Assignment | ALS Vs. Healthy control p-Value ANOVA | Mann-Whitney | Welch T-test | Fold Change |
|---|---|---|---|---|---|---|
| 3 | | Fc(6)A2B | 0.768 | 0.974 | 0.768 | −1.05 |
| 4 | | A2G1 | 0.288 | 0.293 | 0.289 | −1.19 |
| | | Fc(6)A2G1 | | | | |
| 5 | | Fc(6)A2BG1 | 0.027 | 0.038 | 0.029 | −1.1 |
| | | A2BG1 | | | | |
| 6 | | A2G2 | 0.797 | 0.717 | 0.797 | +1.04 |
| 7 | | A2BG2 | 0.0027 | 0.004 | 0.0033 | +2.1 |
| 8 | | Fc(6)A2G2 | 0.276 | 0.341 | 0.281 | −1.12 |

TABLE 4-continued

Statistic analyses comparing N$^{297}$-glycans digested from serum IgG of 19 ALS patients and of 24 healthy candidates.

| Peak no. | Structure | Assignment | ANOVA | Mann-Whitney | Welch T-test | Fold Change |
|---|---|---|---|---|---|---|
| 9 | (structure) | Fc(6)A2BG2 | 0.737 | 0.669 | 0.738 | −1.06 |
| 10 | (structure) | A2G2S1 | 0.254 | 0.178 | 0.259 | +1.18 |
| 11 | (structure) | A2G2S2 | 0.473 | 0.622 | 0.474 | +1.15 |
| 12 | (structure) | Fc(6)A2G2S1 | 0.14 | 0.450 | 0.152 | +1.6 |
| 13 | (structure) | Fc(6)A2G2S2 | 0.202 | 0.237 | 0.215 | +2.9 |

(ALS Vs. Healthy control, p-Value)

Fold of change:
(+) assigns that N$^{297}$ glycan amounts in ALS IgG are higher relative to N$^{297}$ glycans from healthy control IgG and
(−) assigns the opposite.
◇ Sialic acid;
■ GlcNAc;
● Galactose;
△ Fucose;
○ Mannose Similar Fc glycans purified from healthy control IgG were observed, as compared to ALS-IgG, except for one significant difference, namely, a galactosylated structure with a bisecting GlcNAc lacking the core fucose (A2BG2, peak no 7) was doubled in ALS-IgG. As well, the A2BG2 structure was significantly (P<0.015) up-regulated in ALS-purified IgG, as opposed to in purified IgG from inflammatory bowel disease or multiple sclerosis patients (FIG. 3A). Moreover, FIG. 3A illustrates the amounts of the A2BG2 structure in pools of healthy controls, ALS, inflammatory bowel disease, and multiple sclerosis patients.

When pooling the individual samples from each examined group and analyzing by NP-HPLC, similar amounts of A2BG2 were observed as compared to individual samples.

To diminish differences of glycan structural alterations with respect to other clinical parameters such as, sex and age, the serum sample by gender or age were regrouped and a Student's t-test analysis was performed. FIGS. 3B and 3C show that A2BG2 amount does not change with respect to gender or age, respectively.

In order to elucidate whether there is an A2BG2 role in determining IgG activity, pooled samples were used. However, as indicated in Table 4, double and triplicate glycan amounts represented in peaks 12 and 13 respectively, were further observed in patient samples, but found insignificantly as compared to healthy samples. Accordingly, patient and healthy samples with similar glycan amounts represented in peaks 12 and 13, were selected to assemble the pools.

Example 2

N-Glycans of ALS-IGG Involvement in ADCC Reactions

The Fc glycan A2BG2 is known to increase IgG coupling with the CD16 receptor on effector cells, thereby enhancing ADCC. Therefore, in order to illustrate the expression of CD16 within microglia, brain tissues of 130-day old G93A-SOD1 mice and wild-type littermates were sectioned. Staining with CD16 and microglial markers showed that CD16 was abundantly expressed by brain tissue of mSOD1 mice and co-expressed with microglia cells at the end-stage of ALS relative to wild-type mice (FIG. 4A). Morphologically, the microglia of the wild-type expressed CD16 at low intensity (yellow spots) and changed their morphology from ramified to amoeboid morphology in mSOD1 mice, whereas CD16 was expressed at the branches and around the cellular body (the small images of wild-type and its counterpart m-SOD1 brain tissues, respectively). The quantitative analysis summarizes the data shown in FIG. 4A and shows that CD16 was significantly over-expressed in mSOD1 brain tissue relative to low expression in wild-type brain tissue (FIG. 4B). Specifically, CD16 was abundantly co-expressed with microglia in brain tissue of mSOD1 relative to that observed in wild-type brain tissue (FIG. 4C).

To investigate whether the elevated amounts of A2BG2 glycan enhance co-localization of ALS-IgG with CD16 and with microglia, pools of IgG purified from healthy candidates or from ALS patients, with and without the Fc N-glycans were used on tissue sections of G93A-SOD1 mouse brains and wild-type littermates. Intact ALS-IgG, with the Fc glycans, were significantly located in mSOD1 brain tissue relative to lower localization of PNGase-F-treated ALS-IgG and of IgG of healthy candidates in mSOD1-matched tissue (FIGS. 5A, B). As well, the observed localization of ALS-IgG in the wild-type brain tissues was lower than observed in mSOD1 brain tissue (FIGS. 5A, B). Importantly, co-localization of ALS-IgG with CD16 in mSOD1 brain tissue was largely detected on cell surface and branches, apparently of microglia cells (FIGS. 5A, C). Double staining verified that intact ALS-IgG co-localized with mSOD1 microglia cells, where the IgG positioned around the microglia cellular body (FIG. 5D) and branches. Approximately, 65% of microglia from total number of microglia per field bound ALS-IgG. However, ALS-IgG were also detected near the nuclei of other cells. These results are in contrast to those observed when using PNGase-F-treated ALS-IgG or IgG of healthy samples, on mSOD1-matched sections (FIGS. 5A, C); however, they are similar to those observed on sections of spinal cord tissues (data not shown).

Figure 5E:
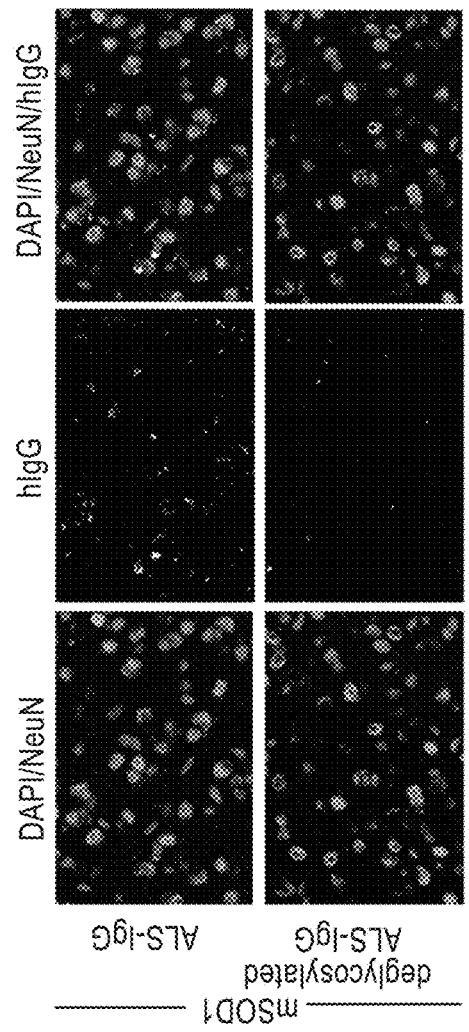
FIG. 5 IgG of ALS patients co-localized with CD16 and microglia cells is located in the immune synapse between microglia and the neuron of G93A-SOD1 brain tissue. Representative confocal microscopic images of brain cortex slices taken from 130-day old G-93A-SOD1 mice and age-matched littermates stained for CD16, hIgG, Iba1, NeuN (neurons) and counterstained with nuclear DAPI. Localization of ALS-IgG before and after PNGase-F treatment and of healthy control-IgG in wild-type and mSOD1 brain tissues. The boxed area is a high magnification of CD16- and intact ALS-IgG-positive cell (A). Histogram of ALS-IgG accumulation before and after PNGase-F treatment and of IgG from healthy control in mSOD1 brain slices (B), Histogram of ALS-IgG before and after PNGase-F treatment and of IgG from healthy control co-localized with CD16 in wild-type and mSOD1 brain tissues (C). Co-localization of intact ALS-IgG with microglia in mSOD1 brain tissue (D), and co-localization of ALS-IgG before and after PNGase-F treatment with NeuN in mSOD1 brain tissue (E). The measurements were performed on 5 fields from 3-4 sections per mouse. Error bars indicate means±SD. Asterisks denote the significance of differences relative to deglycosylated ALS-IgG or control-IgG in mSOD1 sections or ALS-IgG in non-SOD1 littermates, *** p<0.005 represents a comparison with a student's t-test.

Staining of neurons by ALS-IgG indicated that IgG are better co-localized in brain tissue of mSOD1 mice as compared with PNGase F-treated ALS-IgG in mSOD1-matched sections (FIG. 5E). This might be attributed to distinctive coupling to CD16.

Taken together, the increased amount of the IgG-A2BG2 glycoform in ALS sera, the CD16 over-expression in tissue sections of G93A-SOD1 mouse brains, and the co-localization of ALS-IgG with CD16 and microglia indicate that N-glycans of ALS-IgG are involved in ADCC reactions.

Neurons can serve as antigenic targets for ALS-derived IgG, and they bind IgG poorly whether samples are derived from healthy controls or from inflammatory bowel disease or multiple sclerosis patient samples.

Figure 6A:
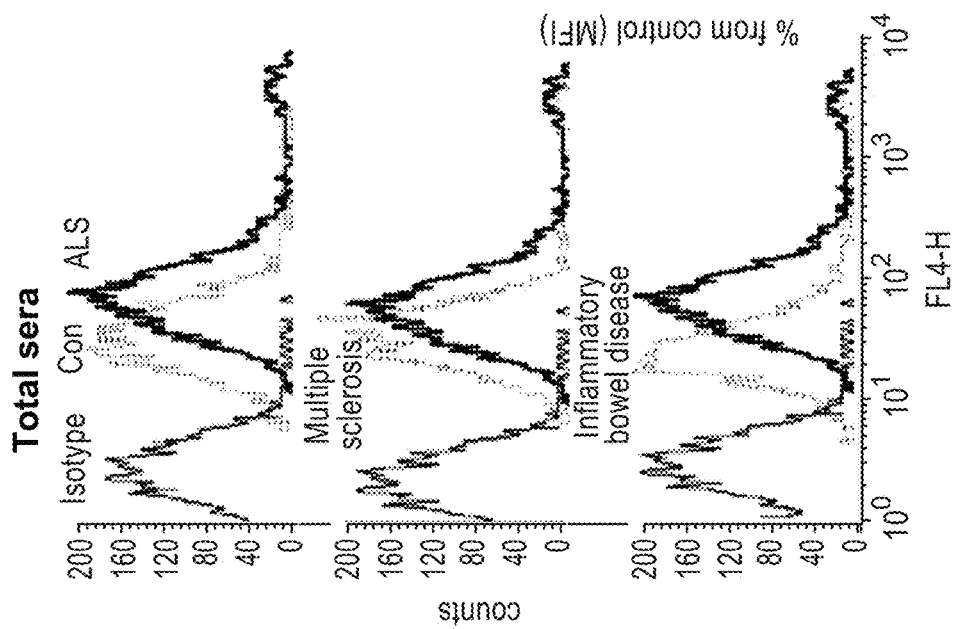
FIG. 6 Coupling of serum IgG to human neuroblastoma cells and to the FcγRIIIA on lymphocytes. Binding of ALS, healthy control (Con), inflammatory bowel disease, and multiple sclerosis patient serum samples (A) or purified ALS-IgG (B) to neuroblastoma cells. Dose-dependent coupling of ALS-IgG to human PANC1, HeLa, and neuroblastoma cells was performed as described above (C). Mean fluorescent intensity (MFI) was calculated relative to control sample containing cells and serum that was free of IgG. Secretion of IFNγ by enriched human peripheral NK cells in response to interactions with pools of ALS, inflammatory bowel disease patients, patients of multiple sclerosis, and healthy control (CON) sera (D). Secretion of IL-2 by BW-CD16 transfectants or BW cells in response to interactions with pools of ALS and healthy control sera (E), and in response to interactions with ALS-IgG and ALS IgG-depleted sera (F). Comparing the specificity of dose-dependent coupling of PNGase F-treated or untreated IgG of ALS patients and of the IgG of healthy volunteers, to CD-16 (G) Data represent the mean±SD of triplicate measurements from independent duplicate experiments. Pools of healthy and patient samples contained a mixture of 4 individual serum samples with similar glycan amounts represented in peaks 12 and 13. Statistical significance, * p<0.005,  p<0.01 and * p<0.05, versus the appropriate controls in each panel.
Figure 6B:
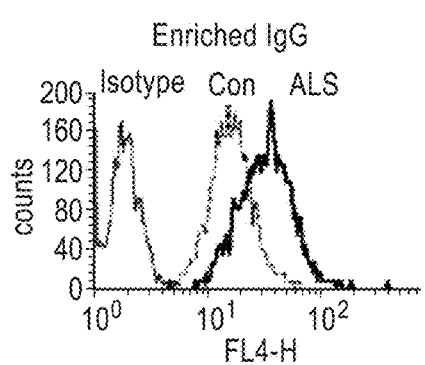
Figure 6C:
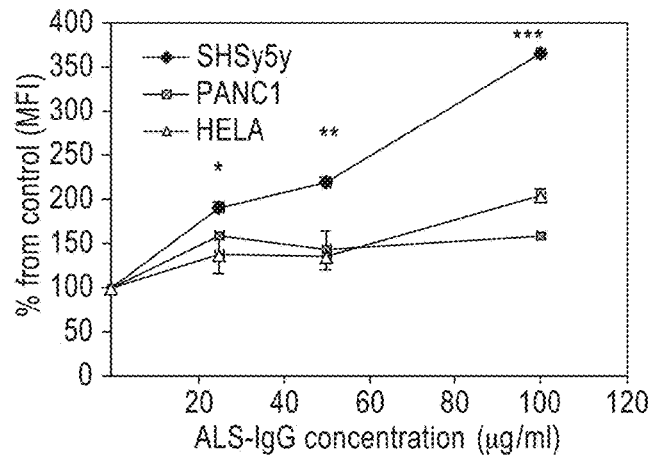

As such, neuroblastoma cells blocked by anti-CD16/CD32 antibodies were incubated with pools of serum samples or with purified IgG and then assessed by FACS. The binding of either purified or unpurified ALS-IgG to the surface of the neuroblastoma cells was elevated, relative to such binding by pools of healthy control (FIGS. 6A, B), inflammatory bowel disease (FIG. 6A) or multiple sclerosis patient IgG (FIG. 6A). Compared to the specificity of ALS-IgG binding by neuroblastoma, HeLa and PANC1 cells revealed significant differences between neuronal and non-neuronal cells (FIG. 6C).

Figure 6D:
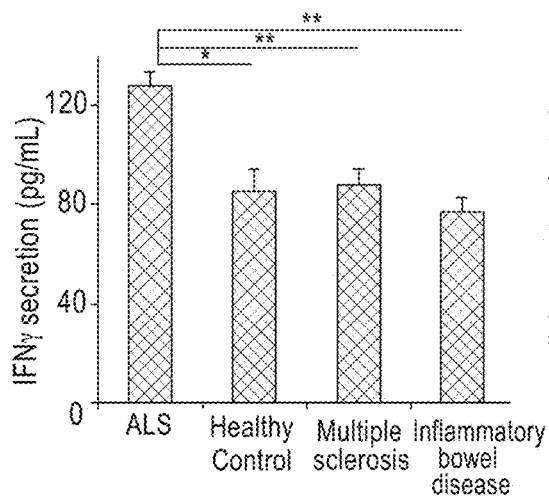
Figure 6E:
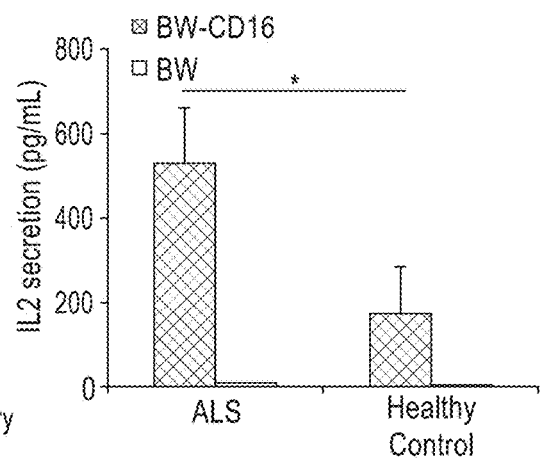
Figure 6F:
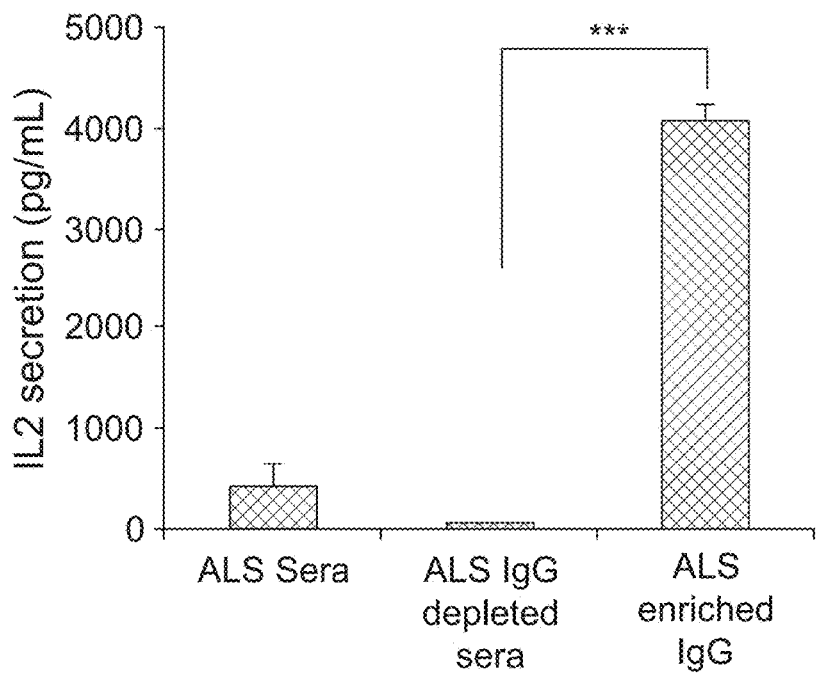
Figure 6G:
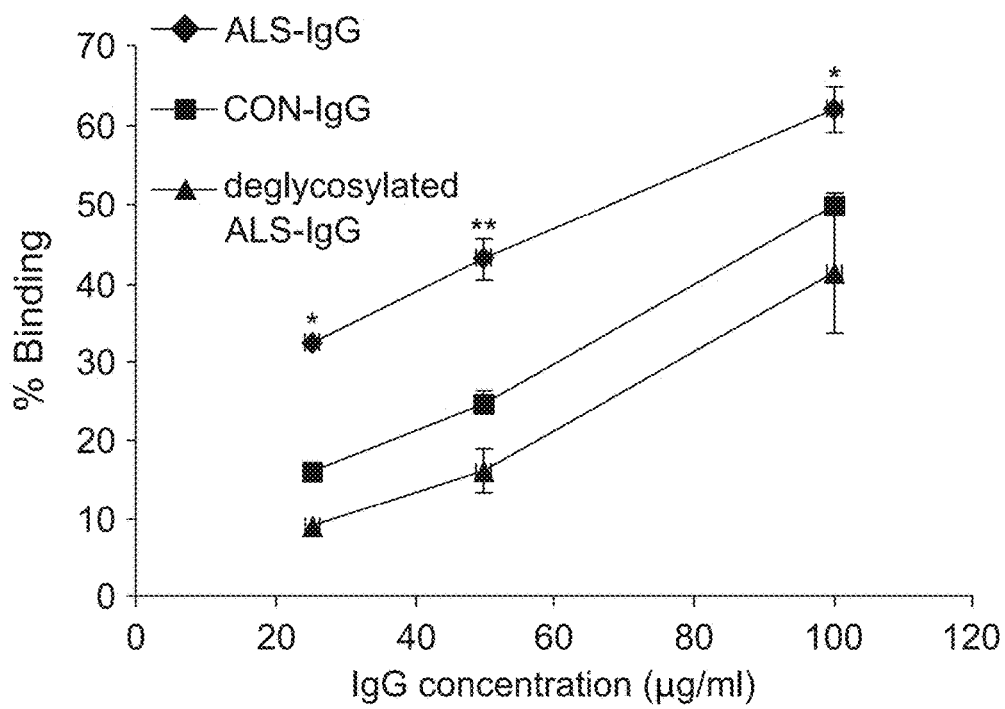

In order to determine whether the elevated amounts of A2BG2 glycan in the Fc domain found in ALS-IgG increased the affinity of these antibodies to CD16, cytokine production and the percentage of IgG binding to CD16 were measured. Pools of serum samples from healthy controls, ALS, from patients with inflammatory bowel disease and from multiple sclerosis patients, containing similar concentrations of IgG were incubated with purified human peripheral NK cells for 18 h. As well, pools of serum samples from healthy controls and ALS or ALS-IgG and ALS IgG-depleted sera were incubated with BW-CD16-transfected or normal BW cells (26), for 18 h. NK cells containing CD16 and BW-CD16 transfectants produced IFNγ and IL-2, respectively, in response to Fc ligand coupling. ELISA results illustrated that NK cells were activated by ALS patient sera to produce augmented amounts of IFNγ, while inflammatory bowel disease patient, multiple sclerosis patient or healthy control sera induced lower IFNγ production (FIG. 6D). Moreover, more than 2-fold the amount of IL-2 was produced by BW-CD16 transfectants in response to ALS patient sera, as compared to healthy control sera, while normal BW cells incubated with any sera did not produce IL-2 (FIG. 6E). In response to purified IgG, BW-CD16 transfectants produced more than 8-fold amount of IL-2, whereas negligible amounts of IL-2 were produced in response to ALS IgG-depleted sera (FIG. 6F). By FACS and several dilutions, examination of the specific coupling to CD16 of PNGase F-treated or untreated ALS-IgG or of IgG of healthy volunteers, revealed significant differences between the IgG containing the A2BG2 glycan to those lacking this glycan (FIG. 6G).

Figure 7A:
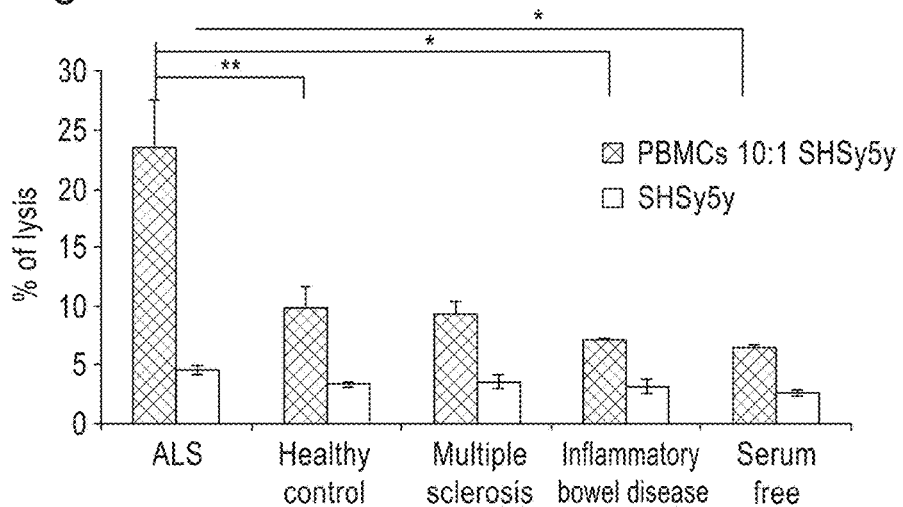
FIG. 7 Killing human neuroblastoma cells through the ADCC pathway. ADCC was performed using human neuroblastoma as target cells, PBMCs as effector cells, and pools of serum samples of ALS, healthy control, inflammatory bowel disease patients, and multiple sclerosis patients as IgG sources. Neuroblastoma cells were also incubated with IgG pools from the different serum sources without co-culturing PBMCs, or in co-cultures with PBMCs but without IgG (A). FACS results from PBMCs pre-treated with anti-CD16 antibodies (B, left) and the heavy chain of ALS-IgG before and after PNGase-F treatment in SDS-PAGE and western blot using ECL-FITC lectin (B, right). ADCC mediated by CD16-blocked effector cells or by ALS-IgG after pNGase-F treatment, as compared to the ADCC against neuroblastoma mediated by unblocked effector cells and untreated ALS-IgG (C). Neuroblastoma lysis by CD32- and CD64-positive THP1 cells was mediated by ALS-IgG, IgG of healthy controls, and in serum free of IgG (D). Triple staining of mSOD brain tissue from mice, with NeuN, Iba1, and ALS-IgG demonstrates the localization of intact ALS-IgG in immune synapse (arrow) amongst microglia and neurons (E). Spontaneous lysis was measured in neuroblastoma cultures. Data represent the mean±SD of triplicate measurements from triplicate independent experiments. Pools of healthy and patient samples contained a mixture of 4 individual serum samples with similar glycan amounts represented in peaks 12 and 13. Statistical significance, ** p<0.01, * p<0.05 and NS (Not significant) is represented versus the appropriate controls in each panel.

To illustrate the involvement of ALS-derived IgG in mediating ADCC, cytotoxic assays were performed using human neuroblastoma as target cells, PBMCs as effector cells and pools of healthy controls, ALS, inflammatory bowel disease, and multiple sclerosis patients as IgG sources. 25% lysis was mediated by IgG from ALS patient sera (FIG. 7A), while healthy control, inflammatory bowel disease patient and multiple sclerosis patient sera mediated cytotoxicity of less than 10% (FIG. 7A). 7% lysis was measured in samples of neuroblastoma cells co-cultured with PBMCs and values of less than 5% when neuroblastoma cells were incubated with IgG samples as the spontaneous cell lysis.

Figure 7B:
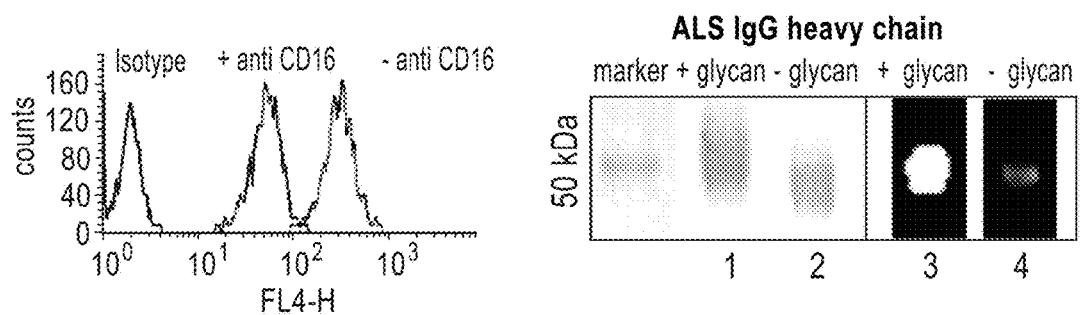
Figure 7C:
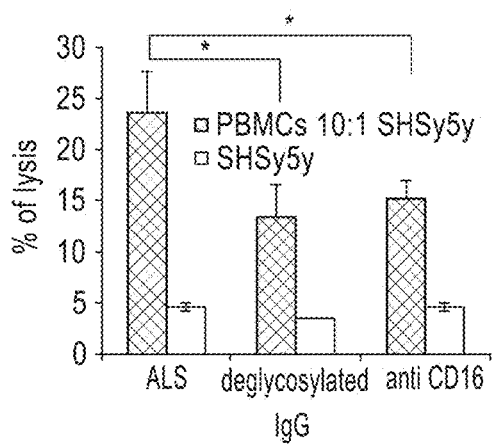

To illustrate the involvement of CD16 in the ADCC reaction mediated by ALS-IgG, PBMCs were blocked with anti-CD16 antibodies and IgG were purified from pool samples. FACS results show a significant decrease in coupling of ALS-IgG to PBMCs, as detected by secondary antibodies (FIG. 7B left). Using the CD16-blocked PBMCs in an ADCC reaction against neuroblastoma cells led to a 40% reduction in the cytotoxic response against the target cells, relative to cell lysis with unblocked PBMCs (FIG. 7C).

Figure 7D:
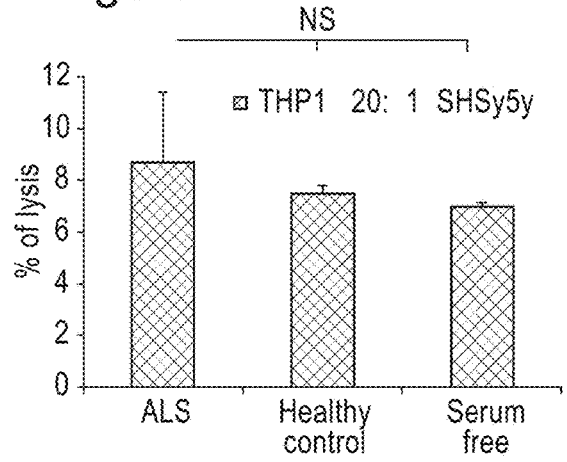

To illustrate the effect of the A2BG2 glycoform on neuroblastoma lysis, N-glycans were removed from ALS-IgG by PNGase F treatment and the heavy chain was assessed by SDS-PAGE and western blot using ECL lectin conjugated to FITC. N-glycans with galactose residues have high affinity to the ECL lectin (27). As can be seen, the heavy chain of ALS-IgG before PNGase F treatment migrated with an average apparent molecular weight of 50 kDa (lane 1) and was well labeled in the western blot protocol (lane 3) (FIG. 7B right). After PNGase F treatment, however, the heavy chain band was shifted to an apparent molecular weight lower than 50 kDa (lane 2), with the fluorescent intensity associated with the immunoblot being quenched (lane 4) (FIG. 7B right). When using ALS-IgG after PNGase F treatment in an ADCC response against neuroblastoma cells, a two-fold decrease in lysis was noted compared to using ALS-IgG bearing N-glycans (FIG. 7C). Opsonizing of ALS-IgG by CD64 and CD32, which either leads to target cell lysis was reversed by using THP1 cells expressing CD32 and CD64 but not CD16 (28), as an alternative to NK cells in the cytotoxic assay (FIG. 7D). These observations indicate that FcγRIIIA on NK cells and the A2BG2 in ALS-IgG are involved in neuroblastoma cell loss.

Figure 7E:
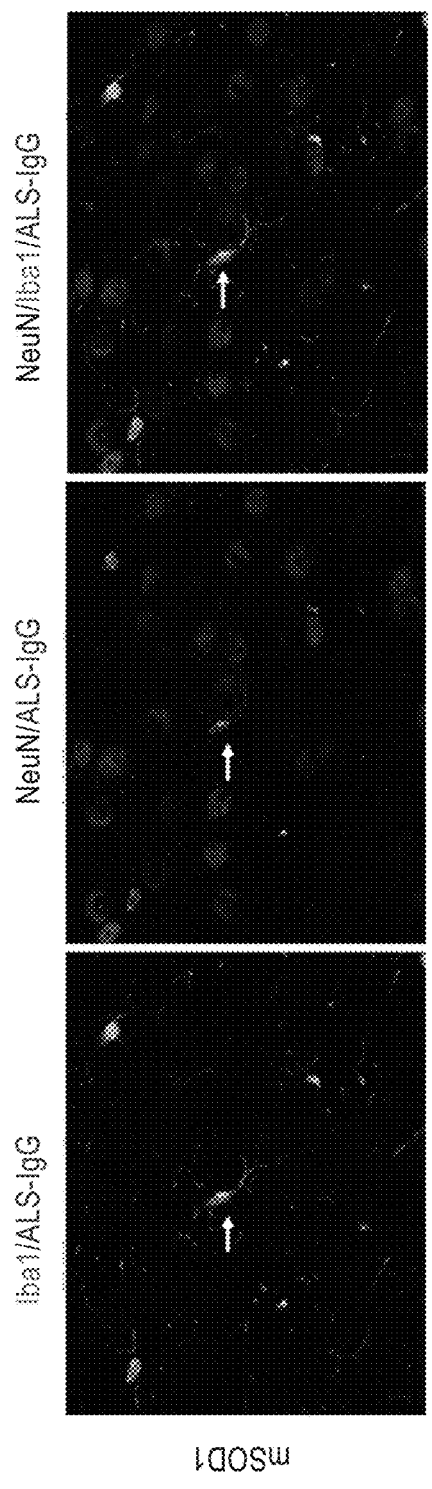

Finally, to demonstrate the feasibility of in vivo ADCC, the localization of intact IgG derived from ALS patients in both neuron and microglia of mSOD1 brain tissue was ascertained, by triple staining. Several ALS-IgG molecules were found to be located in the immune synapse between microglia and the neuron, suggesting the occurrence of ADCC (FIG. 7E). In contrast, such localization was rarely observed in matched-sections when PNGase-F-treated ALS-IgG were used (data not shown). Accordingly, the Fc glycans are involved in IgG deposition in the brain of an ALS animal model and plausibly take part in vivo ADCC.

Figure 8A:
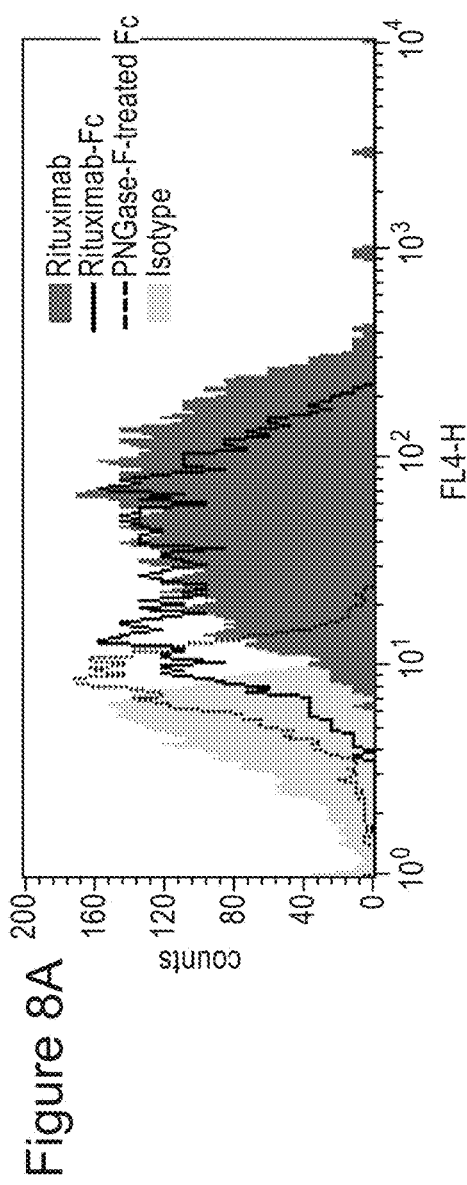
FIG. 8A shows binding of rituximab's Fc to the FcγRIIIA-transfected BW cell line; the figure illustrates evaluation of Fc specificity by coupling of (intact) rituximab or rituximab's Fc and PNGase-F-treated rituximab's Fc domain to CD-16 BW cell line.
Figure 8B:
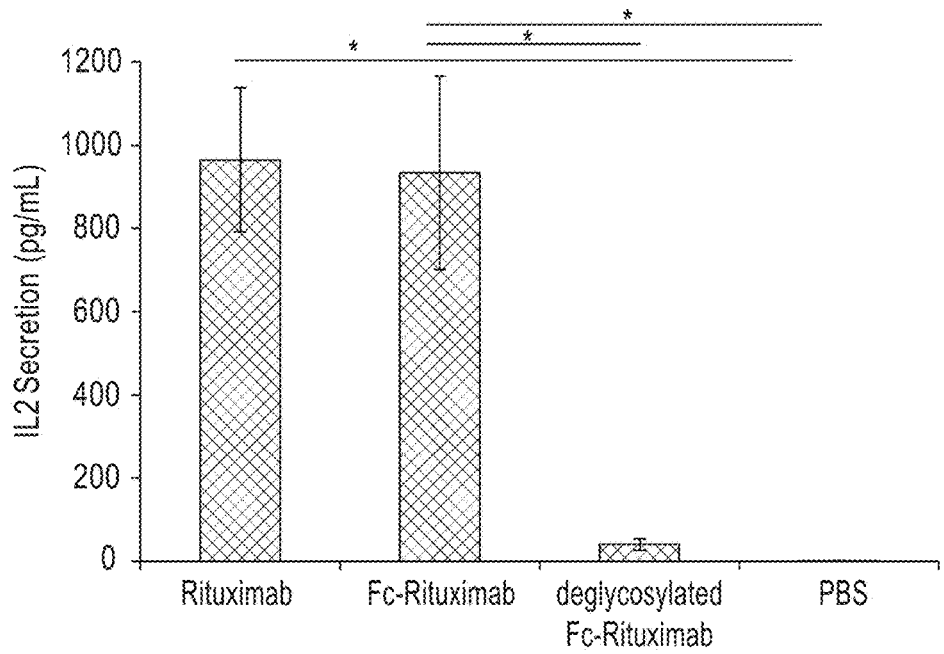
FIG. 8 presents an embodied validation of the methods of this invention.
FIG. 8C shows killing B-cells through the ADCC pathway; ADCC was performed using Daudi B-cells as target cells, PBMCs as effector cells, and intact rituximab as IgG sources. Rituximab's Fc was used as agonist/antagonist. Target cells, effector and IgGs were incubated for 5 h in serum free RPMI.
Figure 8C:
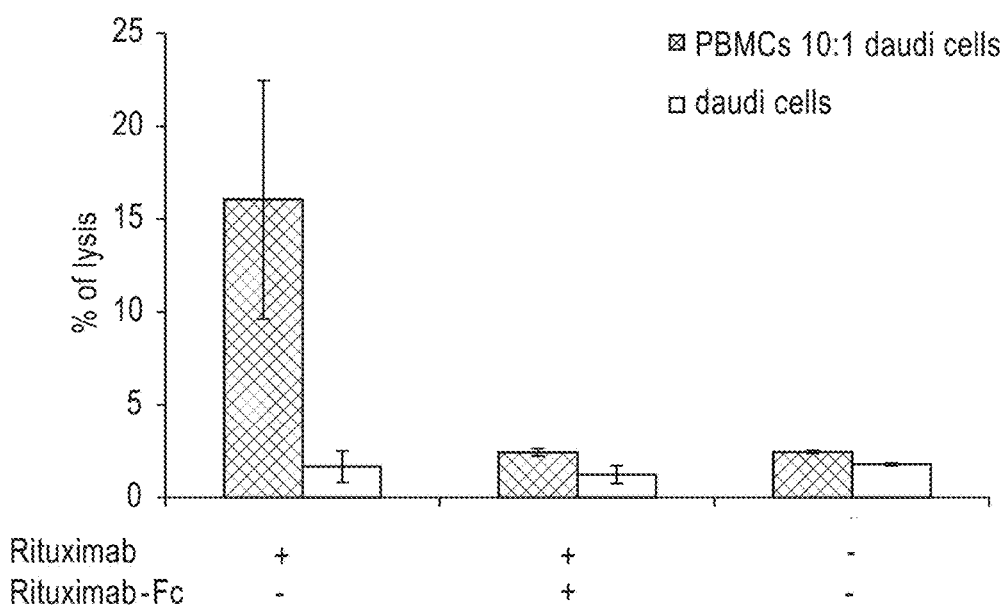

To show the potential of synthetic Fc fragments in inhibiting interactions between IgG and effector cells, a natural Fc fragment was isolated using cysteine protease (papain) that cleaved Fc from the Fab fragment of the commercial drug rituximab. Rituximab is a chimeric monoclonal antibody, which encompasses a human Fab domain with a CD20 antigenic-binding site and a mouse Fc fragment with various glycans in asparagine 297 (Maloney et al. DG, 1997 Anti-CD20 antibody therapy for B-cell lymphomas. N Engl J Med 366(21):2008-16). CD20 is expressed on B-cell surfaces; consequently rituximab is commonly used to destroy malignant B-cells by the mechanisms of ADCC, complement-dependent cytotoxicity and apoptosis. In order to ascertain whether rituximab's Fc favors CD16 binding and papain-digested antibody is unable to opsonize and to mediate lysis, an experimental protocol was developed as described. Rituximab and rituximab's Fc fragment have a high affinity for CD16-transfected (BW) cells (FIG. 8A) and bind CD16 in a similar manner as ALS-IgG. Removing rituximab's Fc glycans decreased the interactions of Fc-CD16. As well, the formation of Fc-CD16 complex by rituximab or its Fc fragment and BW cells stimulated IL-2 secretion in the same order of magnitude as ALS-IgG (FIG. 8B). However, the rituximab Fc fragment blocked ADCC of Daudi B-cell line by CD-16-tranfected BW cells, relative to the complete rituximab drug (FIG. 8C). These data indicate that the Fc, fragment of rituximab is a partial agonist of CD16, allowing cytokine secretion but blocking cell lysis.

The glycan chain synthesis machinery is known to be highly sensitive to the biochemical environment and can change during the course of a disease. In neurodegenerative disorders such as Alzheimer's diseases and Creutzfeldt-Jakob disease, it was found that the glycosylation pattern of several glycoproteins, such as reelin, or acetylcholinesterase, is associated with disease pathogenesis.

The present invention made use of N-glycome analysis of both individual and pooled sera, and demonstrated changes in N-glycan quantity rather than in the presence of unique structures.

Sialylated glycans were significantly increased in ALS patient sera while fucosylated glycans were significantly decreased, as compared to healthy control sera. The alterations detected in ALS patient sera provides a rationale in the subject invention for utilizing the same as disease biomarkers and in the development of new therapeutics for ALS.

In some embodiments of this invention, a method of diagnosing ALS or ALS disease severity relies upon the correlation of glycan expression patterns with disease severity.

IgG-Fc glycans were predicted to contain altered fucosylated and/or sialylated glycans, as observed in the serum N-glycome of patients versus healthy volunteers.

The A2BG2 glycan, which reflects, in part, the reduced fucosylation observed in the serum N-glycome of ALS patients, is an appropriate candidate for diagnostics and targeted therapeutics for ALS.

As shown herein, ALS-derived IgG better mediated ADCC against neuroblastoma cells by human peripheral NK cells, and neuroblastoma lysis was not a consequence of phagocytosis, with cytotoxicity being specifically associated with the ALS patient IgG. Pre-treatment of PBMCs with anti-CD16 antibodies remarkably reduced the ADCC reaction mediated by ALS IgG, while an 18 h incubation of ALS IgG with CD16-transfected BW cells or peripheral NK cells induced IL-2 or IFNγ, respectively.

Furthermore, removing N-glycans from the Fc of ALS IgG by specific cleavage reduced the ADCC reaction.

Thus, neuron loss in ALS is mediated through ADCC with IgG A2BG2 glycan being an important contributor to this pathogenesis pathway.

In addition to the more sialylated and less fucosylated glycans revealed in ALS patient sera relative to healthy control sera, the glycan pattern on the Fc-N$^{297}$ domain of selected IgG serum glycoproteins was shown herein. The distinct structure in the Fc-N$^{297}$ of ALS-IgG as compared to control IgG was found with bisecting and lack of fucose residues on the galactosylated biantennary, A2BG2. Accumulation of IgG in the spinal cord and brain of patients with ALS and in animal models of inherited ALS, the over-expression of CD16 on activated microglia, and the co-localization of largely ALS-IgG with CD16 and with activated microglia in brain tissue from G93A-SOD1 as demonstrated herein, shows that A2BG2 is involved in neuron lysis in ALS.

The involvement of the A2BG2 structure was demonstrated by increased immune activity of CD16-bearing effector cells and by neuroblastoma lysis via ADCC. Moreover, by demonstrating an immunological synapse between brain microglia and neurons of G93A-SOD1 mice, the involvement of IgG Fc-glycan in neuron death in ALS is demonstrated, which is governed by CD16 on microglia cells. Thus, glycans of IgG from ALS patients may serve as a biomarker for the disease.

What is claimed is:

1. A method of treating, delaying progression of, or reducing the severity of amyotrophic lateral sclerosis (ALS) in a subject, said method comprising administering to a subject in need thereof, a therapeutically effective amount of an agent, wherein the therapeutically effective amount is sufficient to interfere with IgG-A2BG2 function or IgG-A2BG2 interaction with CD16 in said subject, wherein the agent is an enzyme which cleaves the A2BG2 glycan from the Fc portion of IgG molecules in said subject, and wherein said agent is specifically targeted to the central nervous system of said subject.

2. The method of claim 1, wherein said subject is further administered adjunct therapies to ameliorate the symptoms of ALS.

3. The method of claim 1, wherein said subject is further administered riluzole.

* * * * *